United States Patent
Schumm et al.

(10) Patent No.: US 6,221,598 B1
(45) Date of Patent: *Apr. 24, 2001

(54) MULTIPLEX AMPLIFICATION OF SHORT TANDEM REPEAT LOCI

(75) Inventors: James W. Schumm; Cynthia J. Sprecher, both of Madison; Ann M. Lins, Lodi, all of WI (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,229

(22) Filed: Jun. 7, 1999

Related U.S. Application Data

(63) Continuation of application No. 08/316,544, filed on Sep. 30, 1994, now abandoned.

(51) Int. Cl.$^7$ .............................. C12Q 1/70; C07H 21/04
(52) U.S. Cl. .................. 435/6; 435/91.1; 435/91.2; 536/23.1; 536/24.31; 536/24.33
(58) Field of Search ........................... 435/6, 91.2, 91.1; 536/24.33, 24.31, 23.1

(56) References Cited

U.S. PATENT DOCUMENTS

| | | |
|---|---|---|
| 4,683,195 | 7/1987 | Mullis et al. . |
| 4,683,202 | 7/1987 | Mullis et al. . |
| 5,364,759 | * 11/1994 | Caskey et al. ........................... 435/6 |
| 5,843,660 | * 12/1999 | Schumm et al. ......................... 435/6 |

FOREIGN PATENT DOCUMENTS

| | | |
|---|---|---|
| WO 93/18177 | 9/1993 | (WO) . |
| WO 93/18178 | 9/1993 | (WO) . |

OTHER PUBLICATIONS

Fregeau et al. "DNA typing with Fluorescently Taggesd SHort Tandem Repeats.." BioTechniques, vol. 15, No. 1, 1993.*
Kimpton et al. "Evaluation of an automated DNA profiling system employing multiplex amplification of four tetrameric STR loci" Int. J. Leg. Med, vol. 106, p. 302–311, 1994.*
Kimpton et al. "Automated DNA profiling Employing Multiplex Amplification of Short Tandem Repeat Loci" PCR Methods and Applications, vol. 3, p. 13–22, 1993.*
Urquhart et al. "Variation in STR sequences a survey of twelve microsatellite loci for use as forensic identification markers" Int. J. Leg. Med, vol. 107, p. 13–20, Aug. 1994.*
Genbank Accession No: V00481, 1983.*
Genbank Accession No: M28420, 1987.*
Genbank Accession No: M21986, 1988.*
Genbank Accession No: M64554, 1990.*
Genbank Accession No: M68651, 1992.*
Genbank Accession No: M25858, 1989.*
Attachment #1, Sequence Alignments for SEQ ID No: 1, 2, 7, 8, 11, 15, 16, 19, 20, 27, and 28.*
Genbank Accession No: M18079, 1987.*
Genbank Accession No: M26434, 1983.*
Genbank Accession No: M87312, 1992.*
Genbank Accession No: M22970, 1986.*
Anker, R., et al., "Tetranucleotide Repeat Polymorphism at the Human Thyroid Peroxidase (hTPO) Locus," *Human Molecular Genetics* (1992) 1(2):137.
Ballabio, A., et al., "Screening for Steroid Sulfatase (STS) Gene Deletions by Multiplex DNA Amplification," *Human Genetics* (1990) 84 (6):571–573.
Bever, R. A., et al.,"Validation and Utilization of Commerically Available STR Multiplexes for Parentage Analysis," *Proceedings from the Fifth International Symposium on Human Identification 1994* (1995) pp. 61–68.
Caetano–Anolles, G., et al., "DNA Amplification Fingerprinting Using Arbitrary Oligonucleotide Primers," *Applied Biochemistry and Biotechnology* (1993) 42:189–200.
Castro, A. et al., (1996) "Multiplex Genetic Typing Of CSF1PO, TPOX and HUMTHO1 Loci in Forensic Samples," *Adv. Forensic Haem.* 6:266–268.
Edwards, A., et al., "DNA Typing with Trimeric and Tetrameric Tandem Repeats: Polymorphic Loci, Detection Systems, and Population Genetics," *Proceedings from the Second International Symposium on Human Identification* (1991) pp. 31–52.
Edwards, M. C., et al., "Multiplex PCR: Advantages, Development, and Applications," *PCR Methods and Applications* (1994) 3:S65–S75.
Eisenberg, M., et al., "PCR for Identity Testing," *Proceedings from the Fifth International Symposium on Human Identification 1994* (1995) pp. 103–107.
Fildes, N. J., et al., "AmpliType® PM Field Trial Results," *Program: Fourth International Symposium on Human Identification* (Sep. 27–29, 1993), p. 119.
Frégeau, C. J., et al., "PCR–Based DNA Identification: A Transition in Forensic Science," *Proceedings from the Fourth International Symposium on Human Identification* (1993) pp. 107–117.
Fuentes, J. J., et al., "Genetic Variation Of Microsatellite Markers D1S117, D11S35, D6S89, APOC2, and D21S168 in the Spanish Population," *Int. J. Leg. Med.* (Spring 1993) 105:271–277.
Garofano, L. et al.. (1998) Italian population data on thirteen short tandem repeat loci. *Forensic Science Int.* 97:53–60. (Abstract—Downloaded from NCBI PubMed).
Greenspoon, S. et al.. (1998) QIAamp spin columns as a method of DNA isolation for forensic casework. *J. Foren. Sci.* 1024–1030.

(List continued on next page.)

Primary Examiner—W. Gary Jones
Assistant Examiner—Jeanine Enewold
(74) Attorney, Agent, or Firm—Michael Best & Friedrich LLP; Grady J. Frenchick; Karen B. King

(57) ABSTRACT

The present invention is directed to the simultaneous amplification of multiple distinct genetic loci using PCR or other amplification systems to determine in one reaction the alleles of each locus contained within the multiplex.

43 Claims, 7 Drawing Sheets

OTHER PUBLICATIONS

Hammond, H., et al., "Personal Identification Via Short Tandem Repeats," *Proceedings from the Third International Symposium on Human Identification* (1992) pp. 163–175.

Hochmeister, M., et al., (1996) "Using Multiplex PCR Amplification and Typing Kits for the Analysis of DNA Evidence in a Serial Killer Case" *J. Forensic Sci.* 41:155–162.

Hochmeister, M. et al., (1995) "Confirmation of the Identity of Human Skeletal Remains using Multiplex PCR Amplification and Typing Kits," *J. Forensic Sci.* 40:701–705.

Hochmeister, M. N., et al., "Swiss Caucasian Population Data and Casework–Applications Using PCR Amplification Kits," *Proceedings from the Fifth International Symposium on Human Identification 1994* (1995) pp. 51–60.

Hochmeister, M. N., et al. "Swiss Population Data on Three Tetrameric Short Tandem Repeat Loci VWA, HUMTH01, and F13A1 Derived Using Multiplex PCR and Laser Fluorescence Detection," *Int. J. Leg. Med.* (1994) 107 (1):34–36.

Holgersson, S., et al., "Fluorescent–Based Typing of the Two Short Tandem Repeat Loci HUMTH01 and HUMACTBP2: Reproducibility of Size Measurements and Genetic Variation in the Swedish Population," *Electrophoresis* (1994) 15:890–895.

Huber, P. and Holtz, J., "Random Priming and Multiplex PCR with Three Short Tandem Repeats for Forensic Casework," *Program: Fourth International Symposium on Human Identification* (Sep. 27–29, 1993) Scottsdale, AZ p. 220.

Hudson, T., et al., "Isolation and Chromosomal Assignment of 100 Highly Informative Human Simple Sequence Repeat Polymorphisms," *Genomics* (1992) 13:622–629.

Kimpton, C., et al., "Automated DNA Profiling Employing Multiplex Amplification of Short Tandem Repeat Loci," *Adv. Forensic Haemogenet* (1994) 5:309–311.

Lee, S. B., et al., "Microwave Extraction, Rapid DNA Quantitation and Fluorescent Detection of Amplified Short Tandem Repeats," *Proceedings from the Fifth International Symposium on Human Identification 1994* (1995) pp. 137–145.

Lorente, M., et al., "Sequential Multiplex Amplification of Genetic Markers from an Individual Sample," *Program: Fourth International Symposium on Human Identification* (Sep. 27–29, 1993) pp. 173–175.

Lygo, J.E., et al. "The Validation of Short Tandem Repeat (STR) Loci for Use in Forensic Casework," *Int. J. Leg. Med.* (1994) 107(2):77–89.

Manam S., et al., "MultiPlex Polymerase Chain Reaction Amplification and Direct Sequencing of Homologous Sequences: Point Mutation Analysis of the ras Genes," *Anal. Biochem.* (1991) 199:106–111.

Micka K. et al.. (1996) "Validation of Multiplex Polymorphic STR Amplification Sets Developed for Personal Identification Applications," *J. For. Sci.* Jul., 582–590.

Moretti, T., et al., (1998) "Enhancement of PCR Amplification Yield and Specificity Using AmpliTaq Gold DNA Polymerase," *Biotechniques.* 25:716–722.

Parkin, B., "The Development of Forensic DNA Profiling in the Metropolitan Police Forensic Science Laboratory," *Proceedings from the Third International Symposium on Human Identification* (1992) pp. 345–356.

Pfitzinger, H., et al., "French Experience in STR Systems: Caucasian Population Data Bases, Automated Fluorescent Quadruplex Typing and Forensic Applications for HUMFESFPS, HUMTH01, HUMVWA31/A and HUMF13A1 Loci," *Proceedings from the Fifth International Symposium on Human Identification 1994* (1995) pp. 85–94.

Prior, T., et al., "A Model for Molecular Screening of Newborns: Simultaneous Detection of Duchenne/Becker Muscular Dystrophies and Cystic Fibrosis," *Clin. Chem.* (1990) 36(10):1756–1759.

Promega, "GenePrint Fluorescent STR Systems," *Technical Manual TMD006* (Dec. 1994).

Promega, "GenePrint STR Systems," *Technical Manual TMD004* (Oct. 1994).

Rosen, B., et al., "Rapid DNA Profiling Using Microsatellites, PCR and Fluorescent DNA Typing," *Proceedings from the Fourth International Symposium on Human Identification* (1993), pp. 228–229.

Sajantila, A., et al., "Application of the Polymerase Chain Reaction in Forensic Medicine," *Proceedings from the Third International Symposium on Human Identification* (1992) pp. 375–381.

Salazar, M., et al., "Genetic Typing of the DQA1*4 Alleles by Restriction Enzyme Digestion of the PCR Product Obtained with the DQ Alpha Amplitype ™ kit," *J. Forensic Sci.* (1993) 39:518–525.

Schmalzing, D. et al., (1999) "Two–color Multiplexed Analysis of Eight Short Tandem Repeat Loci with an Electrophoretic Microdevice," *Anal. Biochem.* 270:148–152.

Schumm, J. W., et al., "Validation of Multiplex Polymorphic STR Amplification Sets Developed for Personal Identification Applications," *Proceedings from the Fifth International Symposium on Human Identification 1994* (1995) p. 49.

Schumm, J. W., et al., "Analysis of Short Tandem Repeats: High Throughput Nonisotopic Methods for Every Laboratory," *Practical Techniques in DNA Analysis of PCR Fragments* (Handout at a Workshop held in Scottsdale Sep. 26, 1993) pp. 41–62, title page, pp. i–v.

Schumm, J. W., et al., "Development of Nonisotopic Multiplex Amplification Sets for Analysis of Polymorphic STR Loci," *Proceedings from the Fourth International Symposium on Human Identification* (1993) pp. 177–187.

Shuber, A. P., et al., "Efficient 12–Mutation Testing in the CFTR Gene: a General Model for Complex Mutation Analysis," *Hum. Mol. Genet.* (1993) 2(2):153–158.

Thomson, J., et al., (1999) "Validation of Short Tandem Repeat Analysis for the Investigation of Cases of Disputed Paternity," *Forensic Sci. Int.* 100:1–16. (Abstract—Downloaded from NCBI PubMed).

Tully, G., et al., "Analysis of 6 VNTR Loci by 'Multiplex' PCR and Automated Fluorescent Detection," *Human Genet.* (Spring 1993) 92:554–562.

Williamson, R., et al., "Report of the DNA Committee and Catalogues of Cloned and Mapped Genes and DNA Polymorphisms," *Cytogenet Cell Genet* (1990) 55:457–778.

Schumm, J., et al., "Construction and Use of Allelic Ladders for the STR Systems HUMTH01, HUMCSF1P0 and HUMFESFPS," *Second International Symposium on the Forensic Aspects of DNA Analysis,* Forensic Science Research and Training Center FBI Academy, Quantico, VA, pp. 12–13 and Abstract (1993).

Puers, C., et al., "Identification of Repeat Sequence Heterogeneity at the Polymorphic Short Tandem Repeat Locus HUMTH01[AATG]$_n$ and Reassignment of Alleles in Population Analysis by Using a Locus–specific Allelic Ladder", *Am. J. Hum. Genet.* 53:953–958 (Oct. 1993).

Huckenbeck, W., et al,. "German Data on the HUJMVWA31 locus," *Anthrop. Anz.,* Jg. 54 1: 1–6 (Stuttgart, Mar. 1996).

Morral, N. and Estivill, X., "Short Communication—Multiplex PCR Amplification of Three Microsatellites within CFTR Gene", *Genomics,* 13: 1362–1364 (1992).

Gibbs, R., et al., "Multiplex DNA Deletion Detection and Exon Sequencing of the Hypoxanthine Phophoribosyltransferase Gene in Lesch—Nyhan Families", *Genomics,* 7: 235–244 (1990).

Huang, T., et al., "Genetic Mapping of four Dinucleotide Repeat Loci, DXS453, DXS458, DXS454, and DXS424, on the X Chromosome Using Multiplex Polymerase Chain Reaction", *Genomics,* 13: 375–380 (1992).

\* cited by examiner

HUMCSF1PO

HUMTPOX

HUMTHOI

HUMCSF1PO

HUMTPOX

HUMTHOI

HUMVWFA31

HUMHPRTB

HUMFESFPS

HUMVWFA31

HUMFESFPS

HUMBFXIII
(FI3B)

HUMHPRTB

HUMBFXIII
(FI3B)

HUMPLA2AI

HUMFI3AOI

HUMFABP

HUMCD4

HUMHPRTB

HUMFESFPS

HUMHPRTB

HUMFESFPS

HUMLIPOL

HUMBFXIII
(FI3B)

HUMLIPOL 1 2 3

HUMTHO1

HUMCD4

1 2 3

HUMTPOX

HUMTHO1

MULTIPLEX AMPLIFICATION OF SHORT TANDEM REPEAT LOCI

CROSS REFERENCE TO RELATED APPLICATION

This application is a continuation of U.S. patent application Ser. No. 08/316,544, filed Sep. 30, 1994, now abandoned.

FIELD OF THE INVENTION

The present invention is generally directed to the detection of genetic markers in a genomic system. The present invention is more specifically directed to the simultaneous amplification of multiple distinct polymorphic genetic loci using the polymerase chain reaction or other amplification systems to determine in one reaction the alleles of each locus contained within the multiplex system.

CITED REFERENCES

A full bibliographic citation of the references cited in this application can be found in the section preceding the claims.

DESCRIPTION OF THE PRIOR ART

In recent years, the discovery and development of polymorphic short tandem repeats (STRs) as genetic markers has stimulated progress in the development of linkage maps, the identification and characterization of diseased genes, and the simplification and precision of DNA typing.

Many loci, at least in the human genome, contain a polymorphic STR region. STR loci consist of short, repetitive sequence elements of 3 to 7 base pairs in length. It is estimated that there are 2,000,000 expected trimeric and tetrameric STRs present as frequently as once every 15 kilobases (kb) in the human genome (Edwards et al. 1991; Beckmann and Weber 1992). Nearly half of the STR loci studied by Edwards et al. (1991) are polymorphic, which provides a rich source of genetic markers. Variation in the number of repeat units at a particular locus is responsible for the observed polymorphism reminiscent of VNTR loci (Nakamura et al. 1987) and minisatellite loci (Jeffreys et al. 1985), which contain longer repeat units, and microsatellite or dinucleotide repeat loci (Litt and Luty 1989, Tautz 1989, Weber and May 1989, Beckmann and Weber 1992).

Polymorphic STR loci are extremely useful markers for human identification, paternity testing and genetic mapping. STR loci may be amplified via the polymerase chain reaction (PCR) by employing specific primer sequences identified in the regions flanking the tandem repeat.

Alleles of these loci are differentiated by the number of copies of the repeat sequence contained within the amplified region and are distinguished from one another following electrophoretic separation by any suitable detection method including radioactivity, fluorescence, silver stain, and color.

To minimize labor, materials and analysis time, it is desirable to analyze multiple loci and/or more samples simultaneously. One approach for reaching this goal involves amplification of multiple loci simultaneously in a single reaction. Such "multiplex" amplifications have been described extensively in the literature. Multiplex amplification sets have been extensively developed for analysis of genes related to human genetic diseases such as Duchenne Muscular Dystrophy (Chamberlain et al. 1988, Chamberlain et al. 1989, Beggs et al. 1990, Clemens et al. 1991, Schwartz et al. 1992, Covone et al. 1992), Lesch-Nyhan Syndrome (Gibbs et al. 1990), Cystic Fibrosis (Estivill et al. 1991, Fortina et al. 1992, Ferrie et al. 1992, Morral and Estivill, 1992), and Retinoblasma (Lohmann et al. 1992). Multiplex amplification of polymorphic microsatellite markers (Clemens et al. 1991, Schwartz et al. 1992, Huang et al. 1992) and even STR markers (Edwards et al. 1992, Kimpton et al. 1993, Hammond et al. 1994) have been described.

These amplified products are generally separated by one of several methods of electrophoresis known to those skilled in the art. Several well-known methods of detection of the amplified products have also been described. While ethidium bromide staining of amplified fragments is employed in some cases, in others it is preferred to use methods which label only one of the two strands of the amplified material. Examples of this include radioactive or fluorescent labeling of one of the two primers prior to the amplification of a locus. One of the more sophisticated approaches to detection is the use of different fluorescent labels to allow detection of amplified materials representing different loci, but existing in the same space following electrophoresis. The products of the different loci are differentiated with the use of filters, which allow visualization of one fluorescent label at a time.

Reference is made to International Publications WO 93/18177 and WO 93/18178 to Fortina et al., which are directed to methods and kits for diagnosing diseases such as Cystic Fibrosis and β-thalassemia, respectively, using an allele-specific multiplex polymerase chain reaction system. According to Fortina et al., multiplex PCR has also been used for simultaneous amplification of multiple target sequences, permitting mutant allele scanning using two lanes of an agarose gel.

Ballabio et al. (1991), disclose a single-tube, multiplex allele specific PCR test using two different dye-tagged fluorescent primers for detection of the ▲F508 cystic fibrosis mutation.

While there are multiplex amplification procedures for specific loci, the use of multiplex amplification procedures is greatly desired for the detection of alleles in other types of loci such as specific STR loci.

SUMMARY OF THE INVENTION

It is therefore an object of the present invention to provide a method for the simultaneous amplification of multiple distinct polymorphic STR loci using PCR or other amplification systems to determine, in one reaction, the alleles of each locus contained within the multiplex. These combinations of specific loci into multiplexes have not been heretofore shown.

It is also an object of the present invention to provide a method and a kit specific for multiplex amplifications comprising specified loci.

These and other objects are addressed by the present invention which is directed to a method of simultaneously analyzing or determining the alleles present at each individual locus of each multiplex. This method comprises the steps of (1) obtaining at least one DNA sample to be analyzed, wherein the DNA sample has at least two loci which can be amplified together; (2) amplifying the STR sequences in the DNA sample; and (3) detecting the amplified materials in a fashion which reveals the polymorphic nature of the systems employed.

The present invention is also directed to a method of simultaneously analyzing multiple STR sequences wherein at least one of the loci is selected from the group consisting of: HUMCSF1PO, HUMTPOX, HUMVWFA31, HUMFESFPS, HUMBFXIII (F13B), HUMLIPOL, HSAC04 (ACTBP2), HUMCYP19, HUMPLA2A1, HUMAPOA2, HUMCD4, HUMF13A01 and HUMMYOPK (Myotonic).

Specifically, the present invention is directed to a method of simultaneously analyzing multiple STR sequences in the following groups of loci: HUMTH01 and HUMCSF1PO; HUMTH01 and HUMCD4; HUMTH01 and HUMTPOX; HUMF13A01 and HUMFABP; HUMF13A01 and HUMMYOPK (Myotonic); HUMF13A01 and HUMBFXIII (F13B); HUMBFXIII (F13B) and HUMFESFPS; HUMBFXIII (F13B) and HUMLIPOL; HUMHPRTB and HUMFESFPS; HSAC04 (ACTBP2) and HUMCYP19; HUMCSF1PO, HUMTPOX and HUMTH01; HUMHPRTB, HUMFESFPS and HUMVWFA31; HSAC04 (ACTBP2), HUMCYP19 and HUMPLA2A1; HSAC04 (ACTBP2) and HUMFABP; HUMAPOA2, HUMCYP19 and HUMPLA2A1; HUMCD4, HUMCSF1PO and HUMTH01; HUMCYP19, HUMFABP and HUMPLA2A1; HUMCYP19, HUMHPRTB and HUMPLA2A1; HUMF13A01, HUMFABP and HUMCD4; HUMHPRTB, HUMFESFPS and HUMLIPOL; HUMF13A01, HUMFABP and HUMCD4; HUMHPRTB, HUMBFXIII (F13B) and HUMPLA2A1; HUMHPRTB, HUMBFXIII (F13B) and HUMTPOX; HUMHPRTB, HUMBFXIII (F13B) and HUMFESFPS; HUMCSF1PO, HUMTPOX and HUMCD4; HUMHPRTB, HUMFESFPS and HUMMYOPK (Myotonic); HUMCSF1PO, HUMTH01 and HUMCD4; HUMCSF1PO, HUMTH01 and HUMVWFA31; HUMHPRTB, HUMBFXIII (F13B) and HUMLIPOL; HUMCSF1PO, HUMTPOX, HUMTH01 and HUMVWFA31; HUMHPRTB, HUMFESFPS, HUMBFXIII (F13B) and HUMLIPOL; HUMCSF1PO, HUMTPOX, HUMTH01 and HUMCD4; and HUMCSF1PO, HUMTH01, HUMTPOX and HUMCD4.

The present invention provides a high throughput method for the detection and analysis of polymorphic genetic markers using specific combinations of loci and specified conditions. By selection of the appropriate detection method, the process can be used in laboratories which have only a power supply and a standard apparatus for polyacrylamide gel electrophoresis or those which have the latest in equipment for fluorescent gel scanning, e.g., FluorImager™ –575 (Molecular Dynamics, Sunnyvale, Calif.). Thus, the process of the present invention is adaptable for a variety of uses and laboratories.

The approach as specified in the present invention produces a savings in time, labor and materials in the analysis of loci contained within the multiplexes. The process of the present invention includes all the requisite primers, allowing between two and four or more loci to be amplified together in one amplification tube instead of amplifying each locus independently.

The present invention has specific use in the field of forensic analysis, paternity determination, monitoring of bone marrow transplantation, linkage mapping, and detection of genetic diseases and cancers.

These and other aspects of the present invention will become evident upon reference to the following detailed description of the invention and the attached drawings and photographs.

DETAILED DESCRIPTION OF THE INVENTION

Figure 1:
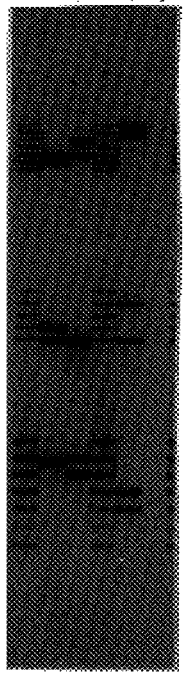
FIG. 1 is a photograph illustrating the simultaneous amplification of three loci: HUMCSF1PO, HUMTPOX and HUMTH01, with the amplified products of each locus shown migrating next to the corresponding allelic ladder for ease of interpretation in Example 1.

The following definitions are intended to assist in providing a clear and consistent understanding of the scope and detail of the terms:

Allelic ladder: a standard size marker consisting of amplified alleles from the locus.

Allele: a genetic variation associated with a segment of DNA, i.e., one of two or more alternate forms of a DNA sequence occupying the same locus.

Biochemical nomenclature: standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP).

DNA polymorphism: the condition in which two or more different nucleotide sequences coexist in the same interbreeding population in a DNA sequence.

Locus (or genetic locus): a specific position on a chromosome. Alleles of a locus are located at identical sites on homologous chromosomes.

Locus-specific primer: a primer that specifically hybridizes with a portion of the stated locus or its complementary strand, at least for one allele of the locus, and does not hybridize efficiently with other DNA sequences under the conditions used in the amplification method.

Polymerase chain reaction (PCR): a technique in which cycles of denaturation, annealing with primer, and extension with DNA polymerase are used to amplify the number of copies of a target DNA sequence by $>10^6$ times. The polymerase chain reaction process for amplifying nucleic acid is covered by U. S. Pat. Nos. 4,683,195 and 4,683,202, which are incorporated herein by reference for a description of the process.

Polymorphism information content (PIC): a measure of the amount of polymorphism present at a locus (*Botstein* et al., 1980). PIC values range from 0 to 1.0, with higher values indicating greater degrees of polymorphism. This measure generally displays smaller values than the other commonly used measure, i.e., heterozygosity. For markers that are highly informative (heterozygosities exceeding about 70%), the difference between heterozygosity and PIC is slight.

Primary reaction: initial reaction using the purified human genomic DNA as template for the PCR.

Primers: two single-stranded oligonucleotides or DNA fragments which hybridize with opposing strands of a locus such that the 3' termini of the primers are in closest proximity.

Primer pair: two primers including primer 1 that hybridizes to a single strand at one end of the DNA sequence to be amplified and primer 2 that hybridizes with the other end on the complementary strand of the DNA sequence to be amplified.

Primer site: the area of the target DNA to which a primer hybridizes.

Secondary reaction: reamplification with the same or different primer pair using a dilution of the primary reaction as template for the PCR.

Construction of the Multiplex System

Prior to constructing the multiplex system, an appropriate set of loci, primers, and amplification protocols must be selected such that amplification generates fragments such that alleles of the various loci do not overlap in size or, when such overlap occurs, fragments representing different loci are detectable by separate means. In addition, the selected loci must be compatible for use with a single amplification protocol. The specific combinations of loci described herein are unique in this application. Combinations of loci may be rejected for either of these reasons, or because, in combination, one or more of the loci do not produce adequate product yield, or fragments which do not represent authentic alleles are produced in this reaction.

Successful combinations are generated by trial and error of locus combinations and by adjustment of primer concentrations to identify an equilibrium in which all included loci may be amplified.

Of particular importance in the multiplex system is the size range of amplified alleles produced from the individual loci which will be analyzed together. For ease of analysis with current technologies, systems which can be detected by amplification of fragments smaller than 500 bases were preferably selected.

The following multiplex combinations have been developed and are considered ideal combinations for use in the present system:

1. HUMTH01 and HUMCSF1PO;
2. HUMTH01 and HUMCD4;
3. HUMTH01 and HUMTPOX;
4. HUMF13A01 and HUMFABP;
5. HUMF13A01 and HUMMYOPK (Myotonic);
6. HUMF13A01 and HUMBFXIII (F13B);
7. HUMBFXIII (F13B) and HUMFESFPS;
8. HUMBFXIII (F13B) and HUMLIPOL;
9. HUMHPRTB and HUMFESFPS;
10. HSAC04 (ACTBP2) and HUMCYP19;
11. HSAC04 (ACTBP2) and HUMFABP;
12. HUMCSF1PO, HUMTPOX and HUMTH01;
13. HUMHPRTB, HUMFESFPS and HUMVWFA31;
14. HSAC04 (ACTBP2), HUMCYP19 and HUMPLA2A1;
15. HUMAPOA2, HUMCYP19 and HUMPLA2A1;
16. HUMCD4, HUMCSF1PO and HUMTH01;
17. HUMCYP19, HUMFABP and HUMPLA2A1;
18. HUMCYP19, HUMHPRTB and HUMPLA2A1;
19. HUMF13A01, HUMFABP and HUMCD4;
20. HUMHPRTB, HUMFESFPS and HUMLIPOL;
21. HUMF13A01, HUMFABP and HUMCD4;
22. HUMHPRTB, HUMBFXIII (F13B) and HUMPLA2A1;
23. HUMHPRTB, HUMBFXIII (F13B) and HUMTPOX;
24. HUMHPRTB, HUMBFXIII (F13B) and HUMFESFPS;
25. HUMCSF1PO, HUMTPOX and HUMCD4;
26. HUMHPRTB, HUMFESFPS and HUMMYOPK (Myotonic);
27. HUMCSF1PO, HUMTH01 and HUMCD4;
28. HUMCSF1PO, HUMTH01 and HUMVWFA31;
29. HUMHPRTB, HUMBFXIII (F13B) and HUMLIPOL;
30. HUMCSF1PO, HUMTPOX, HUMTH01 and HUMVWFA31;
31. HUMHPRTB, HUMFESFPS, HUMBFXIII (F13B) and HUMLIPOL;
32. HUMCSF1PO, HUMTPOX, HUMTH01 and HUMCD4; and
33. HUMCSF1PO, HUMTH01, HUMTPOX and HUMCD4.

The primers must also be designed so that the size of the resulting amplification products differ in length, thereby facilitating assignment of alleles to individual loci during detection. Inappropriate selection of primers can produce several undesirable effects such as lack of amplification, amplification at multiple sites, primer dimer formation, undesirable interaction of primer sequences from different loci, production of alleles from one locus which overlap with alleles from another, or the need for amplification conditions or protocols for the different loci which are incompatible in a multiplex. The synthesis of the primers is conducted by procedures known to those skilled in the art.

Using Multiplexes of Two Loci to Develop Multiplexes Using More than Two Loci

Once a multiplex containing two loci is developed, it may be used as a core to create multiplexes containing more than two loci. New combinations are created including the first two loci. For example, the core multiplex containing loci HUMTH01 and HUMCSF1PO was used to generate derivative multiplexes of HUMTH01, HUMCSF1PO, and HUMTPOX; HUMTH01, HUMCSF1PO, and HUMCD4; HUMTH01, HUMCSF1PO, and HUMVWFA31; HUMTH01, HUMCSF1PO, HUMVWFA31, and HUMTPOX; and HUMTH01, HUMCSF1PO, HUMCD4, and HUMTPOX. Many other derivative multiplexes can be generated based upon a working multiplex. The derivative multiplexes are, in some sense, routine extensions of the core multiplex.

Preparation of Genomic DNA

All methods of DNA preparation which are compatible with the amplification process for a single locus should be appropriate for multiplex amplification. Many examples of preparation methods have been described in the literature (Patel et al. 1984, Gill et al. 1985). DNA concentrations are measured fluorometrically (Brunk et al. 1979).

Amplification of DNA

Human genomic DNA samples are subjected to PCR amplification using primers and thermocycling conditions specific for each locus. Reference is made to Table 1 for details of the primer sequences. The amplification protocol specific to each multiplex is listed in the specific examples.

| Designation | Primer sequences | Sequence ID Number |
|---|---|---|
| HSAC04 | primer 1: ACA TCT CCC CTA CCG CTA TA | 1 |
| (ACTBP2) | primer 2: AAT CTG GGC GAC AAG AGT GA | 2 |
| HUMAPOA2 | primer 1: GGA GCA GTC CTA GGG CCG CGC CGT | 3 |
| (APOCIII) | primer 2: GTG ACA GAG GGA GAC TCC ATT AAA | 4 |
| HUMCSF1PO | primer 1: AAC CTG AGT CTG CCA AGG ACT AGC | 5 |
|  | primer 2: TTC CAC ACA CCA CTG GCC ATC TTC | 6 |
| HUMCYP19 | primer 1: GCA GGT ACT TAG TTA GCT AC | 7 |
| (CYARP450) | primer 2: TTA CAG TGA GCC AAG GTC GT | 8 |
| HUMCD4 | primer 1: CCA GGA AGT TGA GGC TGC AGT GAA | 9 |
|  | primer 2: TTG GAG TCG CAA GCT GAA CTA GCG | 10 |
| HUMF13A01 | primer 1: GAG GTT GCA CTC CAG CCT TTG CAA | 11 |
|  | primer 2: TTC CTG AAT CAT CCC AGA GCC ACA | 12 |
| HUMBFXIII | primer 1: TGA GGT GGT GTA CTA CCA TA | 13 |
| (F13B) | primer 2: GAT CAT GCC ATT GCA CTC TA | 14 |
| HUMFABP | primer 1: GTA GTA TCA GTT TCA TAG GGT CAC C | 15 |
|  | primer 2: CAG TTC GTT TCC ATT GTC TGT CCG | 16 |
| HUMFESFPS | primer 1: GCT GTT AAT TCA TGT AGG GAA GGC | 17 |
|  | primer 2: GTA GTC CCA GCT ACT TGG CTA CTC | 18 |
| HUMHPRTB | primer 1: ATG CCA CAG ATA ATA CAC ATC CCC | 19 |
| (HPRT-1) | primer 2: CTC TCC AGA ATA GTT AGA TGT AGG | 20 |
| HUMMYOPK | primer 1: GCT CGA AGG GTC CTT GTA GCC GGG | 21 |
| Myotonic | primer 2: GAT AGG TGG GGG TGC GTG GAG GAT | 22 |
| HUMLIPOL | primer 1: CTG ACC AAG GAT AGT GGG ATA TAG | 23 |
|  | primer 2: GGT AAC TGA GCG AGA CTG TGT CT | 24 |
| HUMPLA2A1 | primer 1: GGT TGT AAG CTC CAT GAG GTT AGA | 25 |

-continued

| Designation | Primer sequences | Sequence ID Number |
|---|---|---|
| (PLA-AZ) | primer 2: TTG AGC ACT TAC TAT GTG CCA GGC T | 26 |
| HUMTH01 | primer 1: GTG GGC TGA AAA GCT CCC GAT TAT | 27 |
|  | primer 2: ATT CAA AGG GTA TCT GGG CTC TGG | 28 |
| HUMTPOX | primer 1: ACT GGC ACA GAA CAG GCA CTT AGG | 29 |
|  | primer 2: GGA GGA ACT GGG AAC CAC ACA GGT | 30 |
| HUMVWFA31 | primer 1: GA AAG CCC TAG TGG ATG ATA AGA ATA ATC | 31 |
|  | primer 2: GGA CAG ATG ATA AAT ACA TAG GAT GGA TGG | 32 |

Reference is made to the examples below for additional details of the specific procedure relating to each multiplex. The locus-specific primers include a number of nucleotides which, under the conditions used in the hybridization, are sufficient to hybridize with an allele of the locus to be amplified and to be essentially free from amplification of alleles of other loci. Reference is made to U. S. Pat. 5,192,659 to Simons, which is incorporated herein by reference for a more detailed description of locus-specific primers.

Separation and Detection of DNA Fragments

Following amplification, products are then separated by electrophoresis, e.g., denaturing polyacrylamide gel electrophoresis (Sambrook et al., 1989). Preferred gel preparation and electrophoresis procedures are conducted as described in Example 1. Fragment separation occurs based on size and charge of the sample.

The DNA is then detected by, e.g., silver staining (Bassam et al. 1991). Alternatively, if radioactively-labeled or fluorescently-labeled primers were used for each locus, the products are detected by means available to detect these reporters as known to those skilled in the art. Amplified materials may be detected using any of a number of reporters including, e.g., silver staining, radioisotopes, fluorescers, chemiluminescers and enzymes in combination with detectable substrates.

Individual DNA samples containing amplified alleles are preferably compared with a size standard such as a DNA marker or locus-specific allelic ladder to determine the alleles present at each locus within the sample. The preferred size marker for evaluation of a multiplex amplification containing two or more polymorphic STR loci consists of a combination of allelic ladders for the loci being evaluated.

The preferred size marker for evaluation of a multiplex amplification containing two or more polymorphic STR loci which are generated using fluorescently-labeled primers for each locus consists of a combination of fluorescently-labeled allelic ladders for the loci being evaluated.

Following the construction of allelic ladders for individual loci, they may be mixed and loaded for gel electrophoresis at the same time as the loading of amplified samples occurs. Each allelic ladder co-migrates with alleles in the sample from the corresponding locus.

A permanent record of the data can be generated with the use of electrophoresis duplicating film (STR systems manual #TMD004, Promega Corporation, Madison, Wis.).

Advantage of Fluorescent Detection

With the advent of automated fluorescent imaging, faster detection and analysis of multiplex amplification products can be achieved. For fluorescent analyses, one fluoresceinated primer can be included in the amplification of each locus. Separation of the amplified fragments is achieved in precisely the same manner as with the silver stain detection method. The resulting gel is loaded onto a FluorImager® 575 (Molecular Dynamics, Sunnyvale, Calif.) which scans the gel and digitizes the data in three minutes. The FluorImager® contains an argon laser emitting 488 nm light which sweeps through the gel using a galvanometer-controlled mirror. The light activates fluorescent molecules in its path and they, in turn, emit light of higher wavelength. A filter prohibits passage of the original light, but allows collection of the emitted light by a fiber optic collector. A second filter selected by the user may be inserted between the fiber optic collector and the photomultiplier, allowing detection of specific wavelength bands (or colors) with each scan.

The image has an overall cleaner appearance than that obtained with the silver stain for three reasons. First, only one of the two PCR product strands is labeled with primer, simplifying the two band per allele images of the silver stain. Second, in the silver stain reaction, the entire gel is exposed to silver and prone to silver deposition causing a significant general background. With the fluorescent reporter, only the primer is labeled and the unincorporated primers migrate out of the bottom of the gel prior to detection. Third, some artifact bands of the PCR reaction are plentiful, but contain very little primer.

Because this fluorescent method detects only products with one particular primer, some of these artifacts which appear in silver stain of multiplex amplifications are not detected. In fact, this characteristic has allowed development of the more complex quadriplex as shown in FIG. 2 in place of the triplex shown in FIG. 1.

Kit

The present invention is also directed to kits that utilize the process described. A basic kit includes a container having a locus-specific primer pair (or alternately separate containers containing each primer of a primer pair) for each locus. The kit also includes instructions for use.

Other ingredients may include an allelic ladder directed to each of the specified loci, a sufficient quantity of enzyme for amplification, amplification buffer to facilitate the amplification, loading solution for preparation of the amplified material for gel electrophoresis, human genomic DNA as a control to test that the system is working well, a size marker to insure that materials migrate as anticipated in the gel, and a protocol and manual to educate the user and to limit error in use. The amounts of the various reagents in the kits can be varied depending upon a number of factors, such as the optimum sensitivity of the process. The instructions for use are suitable to enable any analyst to carry out the desired test. It is within the scope of this invention to provide test kits for use in manual applications or test kits for use with automated detectors or analyzers.

EXAMPLES

The following examples are presented to illustrate the advantages of the present invention and to assist one of ordinary skill in making and using the same. The examples are not intended in any way to otherwise limit the scope of the disclosure or protection granted by the patent.

Genomic DNA isolation and quantitation were performed essentially as described by Puers et al., 1993. These methods are generally known to those skilled in the art and are preferred, but not required, for application of the invention.

Amplification products were separated by electrophoresis through a 0.4mm thick 4% denaturing polyacrylamide gel (19:1 ratio of acrylamide to bis-acrylamide) which contained 7 M urea (Sambrook et al., 1989) and was chemically cross-linked to one glass plate (Kobayashi, 1988). DNA samples were mixed with 3 µl loading solution (10 mM NaOH, 95% formamide, 0.05% bromophenol blue, 0.05% xylene cyanol), denatured at 95° C. for 2 min., and chilled on ice prior to loading.

Electrophoresis was performed at 60 W in 0.5× TBE for 1–2 hrs. The DNA was detected by silver staining (Bassam et al., 1991). Permanent images were obtained by exposure to Electrophoresis Duplicating Films (EDF, Kodak, Cat. No. 809 6232). Alternatively, detection can be performed by fluorescent scanning (Schumm et al., 1994) or radioactive detection (Hammond et al., 1994).

Example 1

Silver Stain Detection of Multiplex Amplification of Loci HUMCSF1PO, HUMTPOX, and HUMTH01

In this example, a DNA template (three DNA samples) was amplified at the individual loci HUMCSF1PO, HUMTPOX, and HUMTH01 simultaneously in a single reaction vessel. The PCR amplifications were performed in 50 µl volumes using 25 ng template, 0.03 U Taq DNA Polymerase/µl, 1×STR Buffer (50 mM KCl, 10 mM Tris-HCl (pH 9.0 at 25° C.), 0.1% Triton X-100, 1.5 mM MgCl2 and 200 µM each of dATP, dCTP, dGTP and dTTP), and using a Thermal Cycler 480 (Perkin Elmer Cetus). Amplification protocol 1 (96° C. for 2 min., then 10 cycles of 94° C. for 1 min., 64° C. for 1 min., and 70° C. for 1.5 min., followed by 20 cycles of 90° C. for 1 min., 64° C. for 1 min., 70° C. for 1.5 min.) was employed.

Six amplification primers were used in combination, including 0.2 µM each HUMCSF1PO primers 1 [SEQ. ID. 5] and 2 [SEQ. ID. 6], 0.2 µM each HUMTPOX primers 1 [SEQ. ID. 29] and 2 [SEQ. ID. 30], and 0.6 µM each HUMTH01 primers 1 [SEQ. ID. 27] and 2 [SEQ. ID. 28].

Amplified products were separated by denaturing acrylamide gel electrophoresis on a 40 cm gel for 60–90 min. at 60 W and products were visualized by silver stain analysis according the protocol of Bassam et al. (1991).

Figure 2:
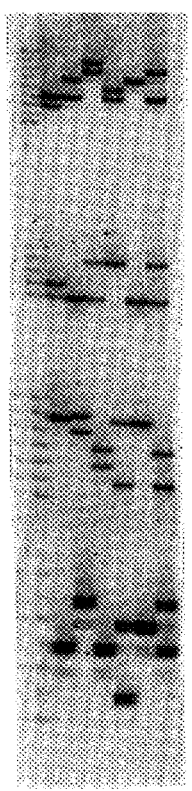
FIG. 2 is a computer image showing the fluorescent detection of multiplex amplification of the loci HUMCSF1PO, HUMTPOX, HUMTH01 and HUMVWFA31 as detected with a FluorImager™ –575 (Molecular Dynamics, Sunnyvale, Calif.) in Example 2.

Reference is made to FIG. 1 which reveals the silver stain detection of the multiplex amplification. Lanes 2, 3, and 5 contain DNA samples simultaneously co-amplified for the loci HUMCSF1PO, HUMTPOX, and HUMTH01. Lanes 1, 4, and 7 contain allelic ladders for the three loci and lane 6 displays a sample without DNA subjected to the same procedures, i.e., a negative control.

Example 2

Fluorescent Detection of Multiplex Amplification of Loci HUMCSF1PO, HUMTPOX, HUMTH01, and HUMVWFA31

In this example, a DNA template was amplified at the individual loci HUMCSF1PO, HUMTPOX, HUMTH01, and HUMVWFA31 simultaneously in a single reaction vessel. The PCR amplifications were performed in 25 µl volumes using 25 ng template, 0.04 U Taq DNA Polymerase/µl, 1×STR Buffer (50 mM KCl, 10 mM Tris-HCl (pH 9.0 at 25° C.), 0.1% Triton X-100, 1.5 mM MgCl2 and 200 µM each of DATP, dCTP, dGTP and dTTP), and using a Thermal Cycler 480 (Perkin Elmer Cetus). Amplification protocol 1, as described in Example 1, was employed. Eight amplification primers were used in combination, including 1 µM each HUMCSF1PO primer 2 [SEQ. ID 6] and fluorescein-labeled primer 1 [SEQ. ID. 5], 0.15 µM each HUMTPOX primer 1 [SEQ. ID. 29] and fluorescein-labeled primer 2 [SEQ. ID. 30], 0.2 µM each HUMTH01 primer 2 [SEQ. ID. 28] and fluorescein-labeled primer 1 [SEQ. ID. 27], and 1 µM each HUMVWFA31 primer 1 [SEQ. ID. 31] and fluorescein-labeled primer 2 [SEQ. ID. 32].

Amplified products were separated by denaturing acrylamide gel electrophoresis on a 32 cm gel for 45 minutes at 40 watts. Detection of the fluorescent signal was achieved using the FluorImager™ 575 (Molecular Dynamics, Sunnyvale, Calif.). Reference is made to FIG. 2 which is a computer image of a FluorImager scan. Lanes 2–7 contain DNA samples simultaneously co-amplified for the loci HUMCSF1PO, HUMTPOX, HUMTH01, and HUMVWFA31. Lane 1 contains allelic ladders for the 4 loci.

Example 3

Multiplex Amplification of Loci HUMHPRTB, HUMFESFPS, and HUMVWFA31

In this example, a DNA template was amplified at the loci HUMHPRTB, HUMFESFPS, and HUMVWFA31 simultaneously in a single reaction vessel. The PCR amplifications were performed in 25 µl volumes using 25 ng template, 0.03 U Taq DNA Polymerase/µl, 1×STR Buffer (described in example 1), and a Thermal Cycler 480 (Perkin Elmer Cetus). Amplification protocol 2 (96° C. for 2 min., then 10 cycles of 94° C. for 1 min., 60° C. for 1 min., and 70° C. for 1.5 min., followed by 20 cycles of 90° C. for 1 min., 64° C. for 1 min., 70° C. for 1.5 min.) was employed. Amplified products were separated by denaturing acrylamide gel electrophoresis on a 32 cm gel for 45 min. at 40 W and products were visualized by silver stain analysis according the protocol of Bassam et al. (supra.). Six primers were used in combination including 0.2 µM each HUMHPRTB primers 1 [SEQ. ID. 19] and 2 [SEQ. ID. 20], 1.5 µM each HUMFESFPS primers 1 [SEQ. ID. 17] and 2 [SEQ. ID. 18], and 1 µM each HUMVWFA31 primers 1 [SEQ. ID. 31] and 2 [SEQ. ID. 32].

Figure 3:
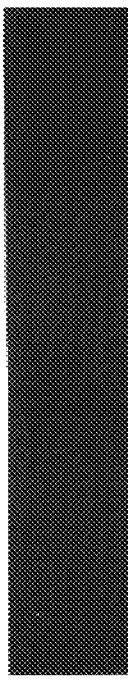
FIG. 3 is a photograph showing the silver stain detection of the multiplex amplification in Example 3.

Reference is made to FIG. 3 which reveals the silver stain detection of the multiplex amplification. Lanes 2–6 contain DNA samples simultaneously co-amplified for the loci HUMHPRTB, HUMFESFPS, and HUMVWFA31. Lanes 1 and 7 contain allelic ladders for the 3 loci.

Example 4

Fluorescent Detection of Multiplex Amplification of Loci HUMHPRTB, HUMFESFPS, HUMBFXIII (F13B), and HUMLIPOL In this example, a DNA template was amplified at the loci HUMHPRTB, HUMFESFPS, HUMBFXIII (F13B), and HUMLIPOL simultaneously in a single reaction vessel. The PCR amplifications and other manipulations were performed as described in Example 2 using amplification protocol 2, as described in Example 3.

Eight primers were used in combination, including 1 $\mu$M each HUMHPRTB primer 2 [SEQ. ID. 20] and fluorescein-labeled primer 1 [SEQ. ID.19], 2.5 $\mu$M each HUMFESFPS primer 2 [SEQ. ID. 18] and fluorescein-labeled primer 1 [SEQ. ID. 17], 1 $\mu$M each HUMBFXIII (F13B) primer 2 [SEQ. ID. 14] and fluorescein-labeled primer 1 [SEQ. ID. 13], and 0.5 $\mu$M each HUMLIPOL primer 2 [SEQ. ID. 24] and fluorescein-labeled primer 1 [SEQ. ID. 23].

Figure 4:
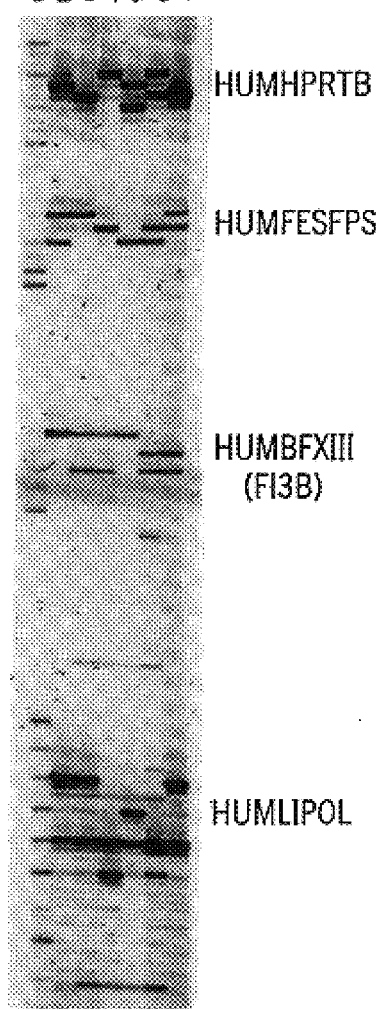
FIG. 4 is a computer image showing the fluorescent detection of multiplex amplification in Example 4.

Reference is made to FIG. 4 which is a computer image of a FluorImager scan. Lanes 2–7 contain DNA samples simultaneously co-amplified for the loci HUMHPRTB, HUMFESFPS, HUMBFXIII (F13B), and HUMLIPOL. Lane 1 contains allelic ladders for the 4 loci.

Example 5

Multiplex Amplification of Loci HSAC04 (ACTBP2) and HUMCYP19

In this example, a DNA template was amplified at the individual loci HSAC04 and HUMCYP19 simultaneously in a single reaction vessel. The PCR amplifications were performed in 15 $\mu$l volumes with 25 ng template, 0.01 U Taq DNA Polymerase/$\mu$l, 1×Taq DNA Polymerase Buffer (50 mM KCl, 10 mM Tris-HCl (pH 9.0 at 25° C.), 0.1% Triton X-100 and 1.5 mM MgCl2) and 200 $\mu$M each of dATP, dCTP, dGTP and dTTP using a Thermal Cycler 480 (Perkin Elmer Cetus). Amplification protocol 2, as described in Example 3, was employed. Amplified products were separated and detected per example 1. Four primers were used in combination, including 1 $\mu$M each HSAC04 (ACTBP2) primers 1 [SEQ. ID. 1] and 2 [SEQ. ID. 2], and 1 $\mu$M each HUMCYP19 primers 1 [SEQ. ID. 7] and 2 [SEQ. ID. 8].

Figure 5:
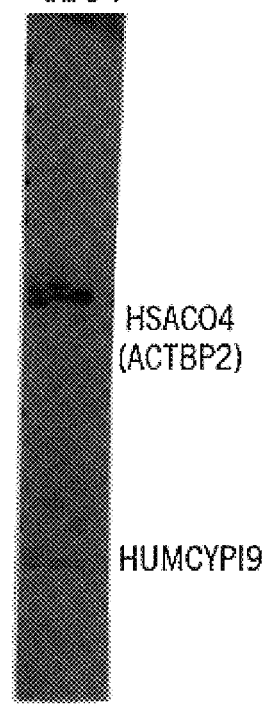
FIG. 5 is a photograph showing the silver stain detection of the multiplex amplification in Example 5.

Reference is made to FIG. 5 which reveals the silver stain detection of the multiplex amplification. Lanes 1–3 contain DNA samples simultaneously co-amplified for the loci HSAC04 (ACTBP2) and HUMCYP19. Lane 4 displays a sample without DNA subjected to the same procedures, i.e., a negative control.

Example 6

Multiplex Amplification of Loci HSAC04 (ACTBP2), HUMCYP19, and HUMPLA2A1

In this example, a DNA template was amplified at the loci HSAC04 (ACTBP2), HUMCYP19, and HUMPLA2A1 simultaneously in a single reaction vessel. The PCR amplifications were performed in 15 $\mu$l volumes with 25 ng template, 0.02 U Taq DNA Polymerase/$\mu$l, 1×Taq DNA Polymerase Buffer (50 mM KCl, 10 mM Tris-HCl (pH 9.0 at 25° C.), 0.1% Triton X-100 and 1.5 mM MgCl2) and 200 $\mu$M each of DATP, dCTP, dGTP and dTTP using a Thermal Cycler 480 (Perkin Elmer Cetus). Amplification protocol 2, as described in Example 3, was employed. Amplified products were separated and detected per example 1. Six primers were used in combination, including 1 $\mu$M each HSAC04 (ACTBP2) primers 1 [SEQ. ID. 1] and 2 [SEQ. ID. 2], 1 $\mu$M each HUMPLA2A1 primers 1 [SEQ. ID. 25] and 2 [SEQ. ID. 26], and 1 $\mu$M each HUMCYP19 primers 1 [SEQ. ID. 7] and 2 [SEQ. ID. 8].

Figure 6:
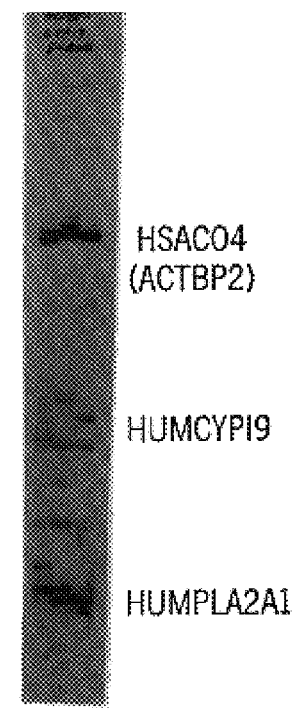
FIG. 6 is a photograph showing the silver stain detection of the multiplex amplification in Example 6.

Reference is made to FIG. 6 which reveals the silver stain detection of the multiplex amplification. Lanes 1–3 contain DNA samples simultaneously co-amplified for the loci HSAC04 (ACTBP2), HUMCYP19, and HUMPLA2A1. Lane 4 displays a sample without DNA subjected to the same procedures, i.e., a negative control.

Example 7

Multiplex Amplification of Loci HSAC04 (ACTBP2) and HUMFABP

In this example, a DNA template was amplified at the loci HSAC04 (ACTBP2) and HUMFABP simultaneously in a single reaction vessel. The PCR amplifications and other manipulations were performed as described in Example 5 using amplification protocol 2, as described in Example 3. Four primers were used in combination, 1 $\mu$M each HSAC04 (ACTBP2) primers 1 [SEQ. ID. 1] and 2 [SEQ. ID. 2], and 1 $\mu$M each HUMFABP primers 1 [SEQ. ID. 15] and 2 [SEQ. ID. 16].

Figure 7:
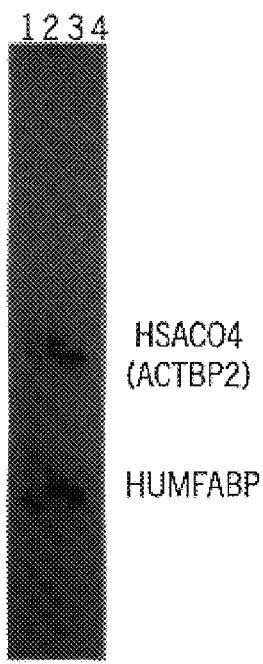
FIG. 7 is a photograph showing the silver stain detection of the multiplex amplification in Example 7.

Reference is made to FIG. 7 which reveals the silver stain detection of the multiplex amplification. Lanes 1–3 contain DNA samples simultaneously co-amplified for the loci HSAC04 (ACTBP2) and HUMFABP. Lane 4 displays a sample without DNA subjected to the same procedures, i.e., a negative control.

Example 8

Multiplex Amplification of Loci HUMAPOA2, HUMCYP19, and HUMPLA2A1

Figure 8:
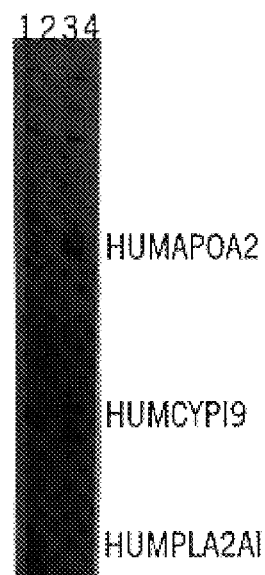
FIG. 8 is a photograph showing the silver stain detection of the multiplex amplification in Example 8.

In this example, a DNA template was amplified at the loci HUMAPOA2, HUMCYP19, and HUMPLA2A simultaneously in a single reaction vessel. The PCR amplifications and other manipulations were performed as described in Example 6 using amplification protocol 2, as described in Example 3. Six primers were used in combination, including 1 $\mu$M each HUMAPOA2 primers 1 [SEQ. ID. 3] and 2 [SEQ. ID. 4], 1 $\mu$M each HUMCYP19 primers 1 [SEQ. ID. 7] and 2 [SEQ. ID. 8], and 1 $\mu$M each HUMPLA2A1 primers 1 [SEQ. ID. 25] and 2 [SEQ. ID. 26]. Reference is made to FIG. 8 which reveals the silver stain detection of the multiplex amplification. Lanes 1 and 3 contain DNA samples simultaneously co-amplified for the loci HUMAPOA2, HUMCYP19, and HUMPLA2A1. Lane 2 contains a DNA sample which failed to amplify and lane 4 displays a sample without DNA subjected to the same procedures, i.e., a negative control.

Example 9

Multiplex Amplification of Loci HUMCD4, HUMCSF1PO, and HUMTH01

In this example, a DNA template was amplified at the loci HUMCD4, HUMCSF1PO, and HUMTH01 simultaneously in a single reaction vessel. The PCR amplifications were performed in 50 $\mu$l volumes with 25 ng template, 0.02 U Taq DNA Polymerase/$\mu$l, 1×Taq DNA Polymerase Buffer (50 mM KCl, 10 mM Tris-HCl (pH 9.0 at 25° C.), 0.1% Triton X-100 and 1.5 mM MgCl2) and 200 μM each of DATP, dCTP, dGTP and dTTP using a Thermal Cycler 480 (Perkin Elmer Cetus). Amplification protocol 1, as described in Example 1, was employed. Amplified products were separated and detected as described in Example 1. Six primers were used in combination, including 1 μM each HUMCD4 primers 1 [SEQ. ID. 9] and 2 [SEQ. ID. 10], 1 μM each HUMCSF1PO primers 1 [SEQ. ID. 5] and 2 [SEQ. ID. 6], and 1 μM each HUMTH01 primers 1 [SEQ. ID. 27] and 2 [SEQ. ID. 28].

Figure 9:
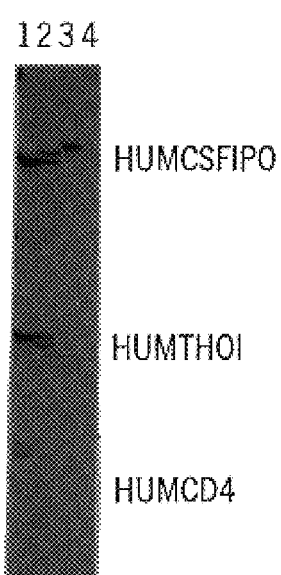
FIG. 9 is a photograph showing the silver stain detection of the multiplex amplification in Example 9.

Reference is made to FIG. 9 which reveals the silver stain detection of the multiplex amplification. Lanes 1–3 contain DNA samples simultaneously co-amplified for the loci HUMCD4, HUMCSF1PO, and HUMTH01. Lane 4 displays a sample without DNA subjected to the same procedures, i.e., a negative control.

Example 10

Multiplex Amplification of Loci HUMCYP19, HUMFABP, and HUMPLA2A1

In this example, a DNA template was amplified at the loci HUMCYP19, HUMFABP, and HUMPLA2A1 simultaneously in a single reaction vessel. The PCR amplifications and other manipulations were performed as described in Example 6 using amplification protocol 2, as described in Example 3. Six primers were used in combination, including 1 μM each HUMCYP19 primers 1 [SEQ. ID. 7] and 2 [SEQ. ID. 8], 1 μM each HUMFABP primers 1 [SEQ. ID. 15] and 2 [SEQ. ID. 16] and 1 μM each HUMPLA2A1 primers 1 [SEQ. ID. 25] and 2 [SEQ. ID. 26].

Figure 10:
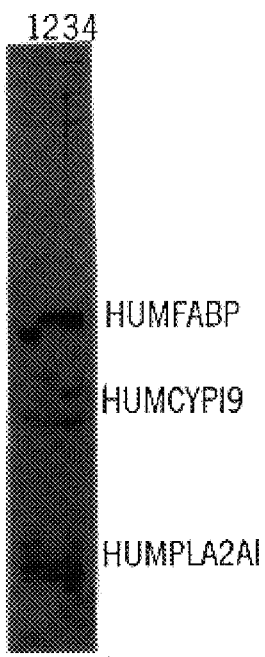
FIG. 10 is a photograph showing the silver stain detection of the multiplex amplification in Example 10.

Reference is made to FIG. 10 which reveals the silver stain detection of the multiplex amplification. Lanes 1–3 contain DNA samples simultaneously co-amplified for the loci HUMCYP19, HUMFABP, and HUMPLA2A1. Lane 4 displays a sample without DNA subjected to the same procedures, i.e., a negative control.

Example 11

Multiplex Amplification of Loci HUMCYP19, HUMHPRTB, and HUMPLA2A1

In this example, a DNA template was amplified at the loci HUMCYP19, HUMHPRTB, and HUMPLA2A1 simultaneously in a single reaction vessel. The PCR amplifications and other manipulations were performed as described in Example 9 using amplification protocol 2, as described in Example 3. Six primers were used in combination, including 1 μM each HUMCYP19 primers 1 [SEQ. ID. 7] and 2 [SEQ. ID. 8], 1 μM each HUMHPRTB primers 1 [SEQ. ID. 19] and 2 [SEQ. ID. 20], and 1 μM each HUMPLA2A1 primers 1 [SEQ. ID. 25] and 2 [SEQ. ID. 26].

Figure 11:
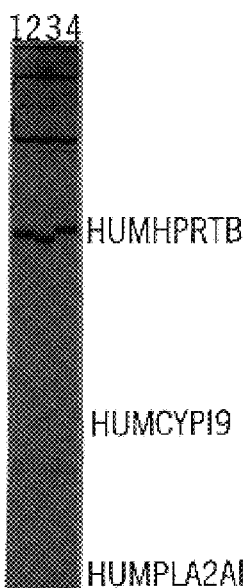
FIG. 11 is a photograph showing the silver stain detection of the multiplex amplification in Example 11.

Reference is made to FIG. 11 which reveals the silver stain detection of the multiplex amplification. Lanes 1–3 contain DNA samples simultaneously co-amplified for the loci HUMCYP19, HUMHPRTB, and HUMPLA2A1. Lane 4 displays a sample without DNA subjected to the same procedures, i.e., a negative control.

Example 12

Multiplex Amplification of Loci HUMF13A01 and HUMFABP

In this example, a DNA template was amplified at the loci HUMF13A01 and HUMFABP simultaneously in a single reaction vessel. The PCR amplifications and other manipu-lations were performed as described in Example 5 using amplification protocol 1, as described in Example 1. Four primers were used in combination, including 1 μM each HUMF13A01 primers 1 [SEQ. ID. 11] and 2 [SEQ. ID. 12], and 1 μM each HUMFABP primers 1 [SEQ. ID. 15] and 2 [SEQ. ID. 16].

Figure 12:
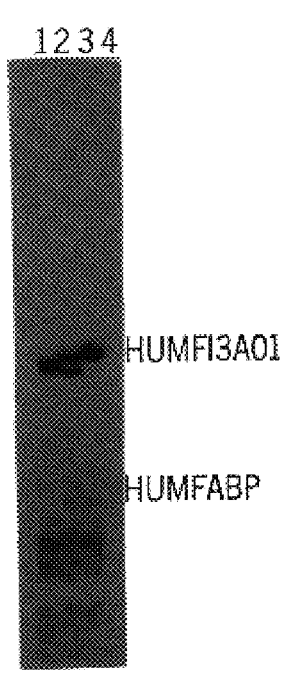
FIG. 12 is a photograph showing the silver stain detection of the multiplex amplification in Example 12.

Reference is made to FIG. 12 which reveals the silver stain detection of the multiplex amplification. Lanes 1–3 contain DNA samples simultaneously co-amplified for the loci HUMF13A01 and HUMFABP. Lane 4 displays a sample without DNA subjected to the same procedures, i.e., a negative control.

Example 13

Multiplex Amplification of Loci HUMBFXIII (F13B) and HUMFESFPS

In this example, a DNA template was amplified at the loci HUMBFXIII (F13B) and HUMFESFPS simultaneously in a single reaction vessel. The PCR amplifications and other manipulations were performed as described in Example 6 using amplification protocol 1, as described in Example 1. Four primers were used in combination, including 1 μM each HUMBFXIII (F13B) primers 1 [SEQ. ID. 13] and 2 [SEQ. ID. 14], and 1 μM each HUMFESFPS primers 1 [SEQ. ID. 17] and 2 [SEQ. ID. 18].

Figure 13:
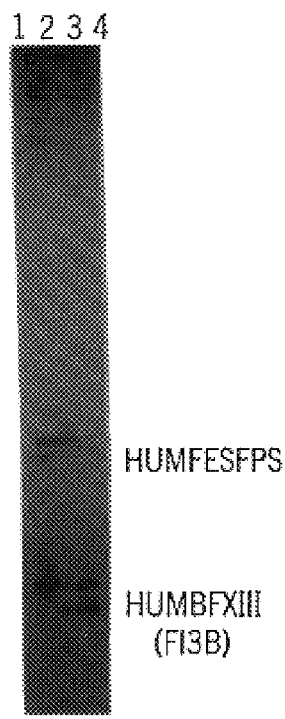
FIG. 13 is a photograph showing the silver stain detection of the multiplex amplification in Example 13.

Reference is made to FIG. 13 which reveals the silver stain detection of the multiplex amplification. Lanes 1–3 contain DNA samples simultaneously co-amplified for the loci HUMBFXIII (F13B) and HUMFESFPS. Lane 4 displays a sample without DNA subjected to the same procedures, i.e., a negative control.

Example 14

Multiplex Amplification of Loci HUMBFXIII (F13B), HUMHPRTB, and HUMPLA2A1

In this example, a DNA template was amplified at the loci HUMBFXIII (F13B), HUMHPRTB, and HUMPLA2A1 simultaneously in a single reaction vessel. The PCR amplifications and other manipulations were performed as described in Example 6 using amplification protocol 2, as described in Example 3. Six primers were used in combination, including 1 μM each HUMBFXIII (F13B) primers 1 [SEQ. ID. 13] and 2 [SEQ. ID. 14], 1 μM each HUMHPRTB primers 1 [SEQ. ID. 19] and 2 [SEQ. ID. 20], and 1 μM each HUMPLA2A1 primers 1 [SEQ. ID. 25] and 2 [SEQ. ID. 26].

Figure 14:
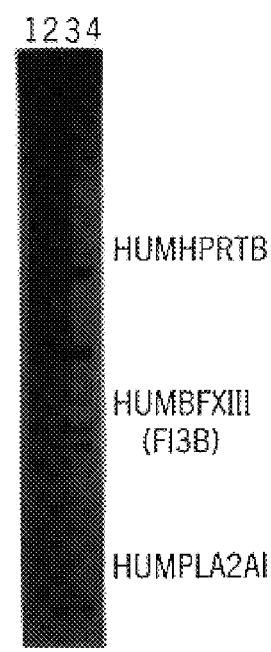
FIG. 14 is a photograph showing the silver stain detection of the multiplex amplification in Example 14.

Reference is made to FIG. 14 which reveals the silver stain detection of the multiplex amplification. Lanes 1–3 contain DNA samples simultaneously co-amplified for the loci HUMBFXIII (F13B), HUMHPRTB, and HUMPLA2A1. Lane 4 displays a sample without DNA subjected to the same procedures, i.e., a negative control.

Example 15

Multiplex Amplification of Loci HUMF13A01, HUMFABP, and HUMCD4

In this example, a DNA template was amplified at the loci HUMF13A01, HUMFABP, and HUMCD4 simultaneously in a single reaction vessel. The PCR amplifications and other manipulations were performed as described in Example 5 using amplification protocol 1, as described in Example 1. Six primers were used in combination, including 1 μM each HUMF13A01 primers 1 [SEQ. ID. 11] and 2 [SEQ. ID. 12], 1 μM each HUMFABP primers 1 [SEQ. ID. 15] and 2 [SEQ. ID. 16], and 1 μM each HUMCD4 primers 1 [SEQ. ID. 9] and 2 [SEQ. ID. 10].

Figure 15:
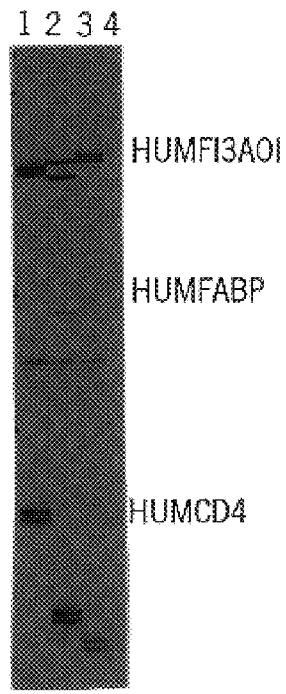
FIG. 15 is a photograph showing the silver stain detection of the multiplex amplification in Example 15.

Reference is made to FIG. 15 which reveals the silver stain detection of the multiplex amplification. Lanes 1–3 contain DNA samples simultaneously co-amplified for the loci HUMF13A01, HUMFABP, and HUMCD4. Lane 4 displays a sample without DNA subjected to the same procedures, i.e., a negative control.

Example 16

Multiplex Amplification of Loci HUMHPRTB and HUMFESFPS

In this example, a DNA template was amplified at the loci HUMHPRTB and HUMFESFPS simultaneously in a single reaction vessel. The PCR amplifications and other manipulations were performed as described in Example 1 using 500–0.5 ng template, 0.02 U Taq DNA Polymerase/μl and amplification protocol 2, as described in Example 3. Four primers were used in combination, including 0.2 μM each HUMHPRTB primers 1 [SEQ. ID. 19] and 2 [SEQ. ID. 20] and 1.5 μM each HUMFESFPS primers 1 [SEQ. ID. 17] and 2 [SEQ. ID. 18].

Figure 16:
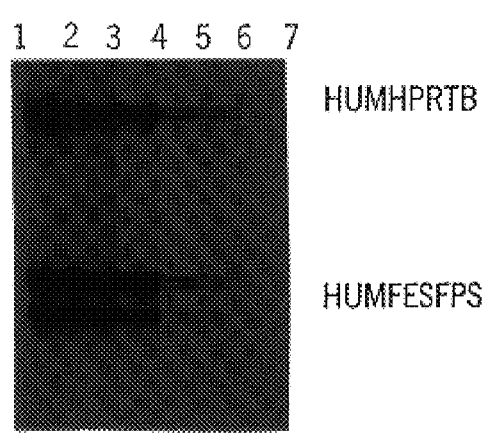
FIG. 16 is a photograph showing the silver stain detection of the multiplex amplification in Example 16.

Reference is made to FIG. 16 which reveals the silver stain detection of the multiplex amplification. Lanes 1–6 contain DNA samples simultaneously co-amplified for the loci HUMHPRTB and HUMFESFPS using 500, 50, 25, 5, 1 and 0.5 ng DNA template. Lane 7 displays a sample without DNA subjected to the same procedures, i.e., a negative control.

Example 17

Multiplex Amplification of Loci HUMHPRTB, HUMFESFPS, and HUMLIPOL

In this example, a DNA template was amplified at the loci HUMHPRTB, HUMFESFPS, and HUMLIPOL simultaneously in a single reaction vessel. The PCR amplifications and other manipulations were performed as described in Example 1 using amplification protocol 2, as described in Example 3. Six primers were used in combination, including 0.4 μM each HUMHPRTB primers 1 [SEQ. ID. 19] and 2 [SEQ. ID. 20], 3 μM each HUMFESFPS primers 1 [SEQ. ID. 17] and 2 [SEQ. ID. 18], and 2 μM each HUMLIPOL primers 1 [SEQ. ID. 23] and 2 [SEQ. ID. 24].

Figure 17:
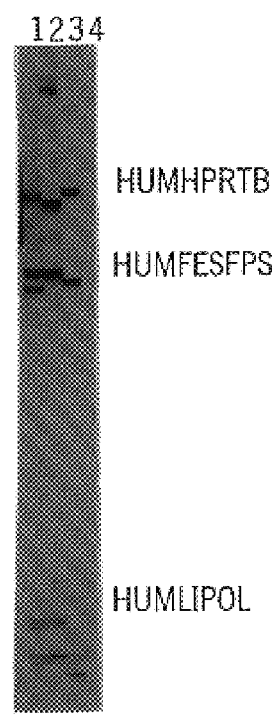
FIG. 17 is a photograph showing the silver stain detection of the multiplex amplification in Example 17.

Reference is made to FIG. 17 which reveals the silver stain detection of the multiplex amplification. Lanes 1–3 contain DNA samples simultaneously co-amplified for the loci HUMHPRTB, HUMFESFPS and HUMLIPOL. Lane 4 displays a sample without DNA subjected to the same procedures, i.e., a negative control.

Example 18

Multiplex Amplification of Loci HUMBFXIII (F13B) and HUMLIPOL

In this example, a DNA template was amplified at the loci HUMBFXIII (F13B) and HUMLIPOL Simultaneously in a single reaction vessel. The PCR amplifications and other manipulations were performed as described in Example 1 using 0.02 U Taq DNA Polymerase/μl and amplification protocol 2, as described in Example 3. Four primers were used in combination, including 1 μM each HUMBFXIII (F13B) primers 1 [SEQ. ID. 13] and 2 [SEQ. ID. 14] and 1 μM each HUMLIPOL primers 1 [SEQ. ID. 23] and 2 [SEQ. ID. 24].

Figure 18:
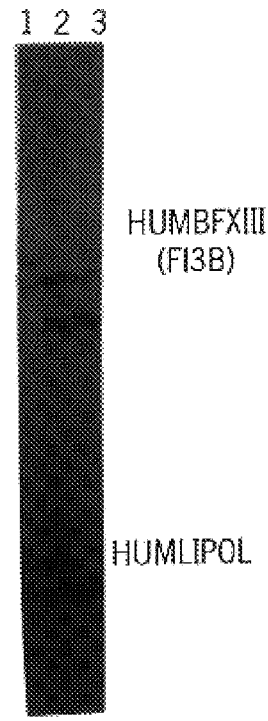
FIG. 18 is a photograph showing the silver stain detection of the multiplex amplification in Example 18.

Reference is made to FIG. 18 which reveals the silver stain detection of the multiplex amplification. Lanes 1–3 contain DNA samples simultaneously co-amplified for the loci HUMBFXIII (F13B) and HUMLIPOL.

Example 19

Multiplex Amplification of Loci HUMHPRTB, HUMTPOX, and HUMBFXIII (F13B)

In this example, a DNA template was amplified at the loci HUMHPRTB, HUMTPOX, and HUMBFXIII (F13B) simultaneously in a single reaction vessel. The PCR amplifications and other manipulations were performed as described in Example 1 using amplification protocol 2, as described in Example 3. Six primers were used in combination, including 1 μM each HUMHPRTB primers 1 [SEQ. ID. 19] and 2 [SEQ. ID. 20], 0.2 μM each HUMTPOX primers 1 [SEQ. ID. 29] and 2 [SEQ. ID. 30], and 2 μM each HUMBFXIII (F13B) primers 1 [SEQ. ID. 13] and 2 [SEQ. ID. 14].

Figure 19:
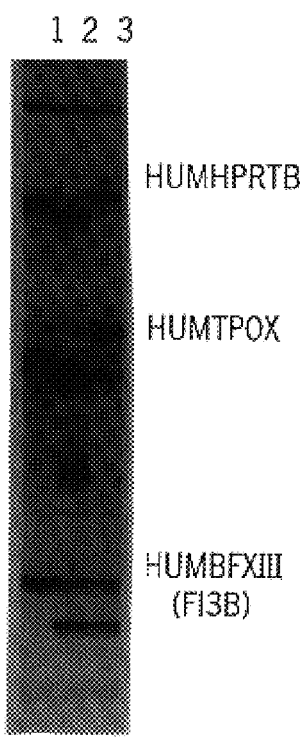
FIG. 19 is a photograph showing the silver stain detection of the multiplex amplification in Example 19.

Reference is made to FIG. 19 which reveals the silver stain detection of the multiplex amplification. Lanes 1–3 contain DNA samples simultaneously co-amplified for the loci HUMHPRTB, HUMTPOX, and HUMBFXIII (F13B).

Example 20

Multiplex Amplification of Loci HUMHPRTB, HUMFESFPS, and HUMBFXIII (F13B)

In this example, a DNA template was amplified at the loci HUMHPRTB, HUMFESFPS, and HUMBFXIII (F13B) simultaneously in a single reaction vessel. The PCR amplifications and other manipulations were performed as described in Example 1 using amplification protocol 2, as described in Example 3. Six primers were used in combination, including 1 μM each HUMHPRTB primers 1 [SEQ. ID. 19] and 2 [SEQ. ID. 20], 2 μM each HUMFESFPS primers 1 [SEQ. ID. 17] and 2 [SEQ. ID. 18], and 2 μM each HUMBFXIII (F13B) primers 1 [SEQ. ID. 13] and 2 [SEQ. ID. 14].

Figure 20:
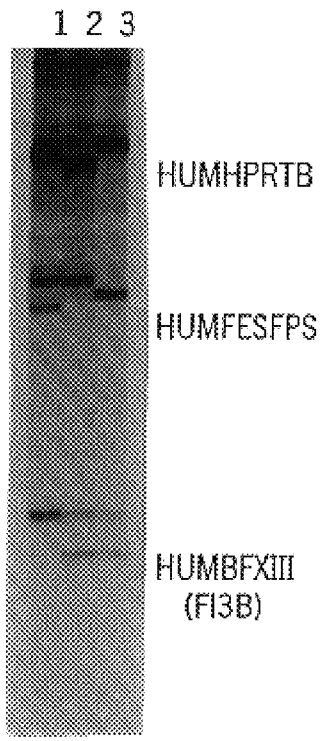
FIG. 20 is a photograph showing the silver stain detection of the multiplex amplification in Example 20.

Reference is made to FIG. 20 which reveals the silver stain detection of the multiplex amplification. Lanes 1–3 contain DNA samples simultaneously co-amplified for the loci HUMHPRTB, HUMFESFPS, and HUMBFXIII (F13B).

Example 21

Multiplex Amplification of Loci HUMCSF1PO, HUMTPOX, and HUMCD4

In this example, a DNA template was amplified at the loci HUMCSF1PO, HUMTPOX, and HUMCD4 simultaneously in a single reaction vessel. The PCR amplifications and other manipulations were performed as described in Example 1 using amplification protocol 1, as described in Example 1. Six primers were used in combination, including 1 μM each HUMCSF1PO primers 1 [SEQ. ID. 5] and 2 [SEQ. ID. 6], 1 μM each HUMTPOX primers 1 [SEQ. ID. 29] and 2 [SEQ. ID. 30], and 1 μM each HUMCD4 primers 1 [SEQ. ID. 9] and 2 [SEQ. ID. 10].

Figure 21:
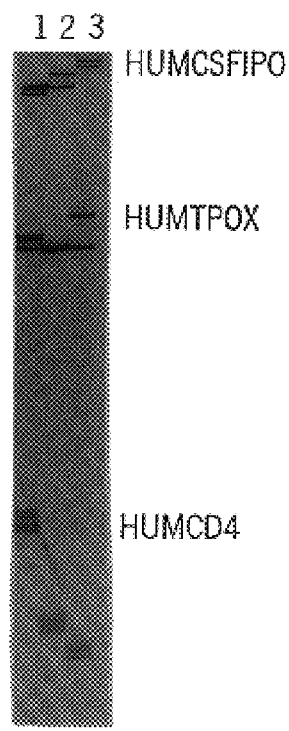
FIG. 21 is a photograph showing the silver stain detection of the multiplex amplification in Example 21.

Reference is made to FIG. 21 which reveals the silver stain detection of the multiplex amplification. Lanes 1–3 contain DNA samples simultaneously co-amplified for the loci HUMCSF1PO, HUMTPOX, and HUMCD4.

Example 22

Multiplex Amplification of Loci HUMHPRTB, HUMFESFPS, and HUMMYOPK (Myotonic)

In this example, a DNA template was amplified at the loci HUMHPRTB, HUMFESFPS, and HUMMYOPK simultaneously in a single reaction vessel. The PCR amplifications and other manipulations were performed as described in Example 1 using amplification protocol 2, as described in Example 3. Six primers were used in combination, including 1 µM each HUMHPRTB primers 1 [SEQ. ID. 19] and 2 [SEQ. ID. 20], 1 µM each HUMFESFPS primers 1 [SEQ. ID. 17] and 2 [SEQ. ID. 18], and 1 µM each HUMMYOPK (Myotonic) primers 1 [SEQ. ID. 21] and 2 [SEQ. ID. 22].

Figure 22:
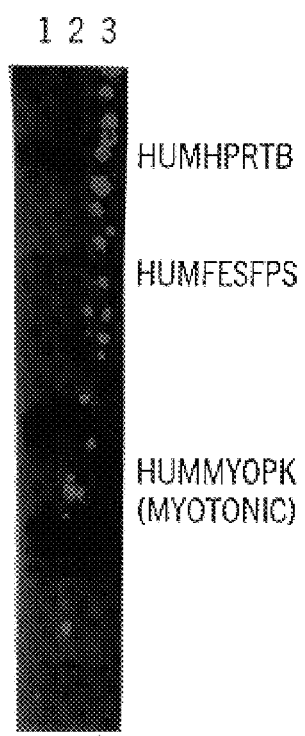
FIG. 22 is a photograph showing the silver stain detection of the multiplex amplification in Example 22.

Reference is made to FIG. 22 which reveals the silver stain detection of the multiplex amplification. Lanes 1–3 contain DNA samples simultaneously co-amplified for the loci HUMHPRTB, HUMFESFPS, and HUMMYOPK (Myotonic).

Example 23

Multiplex Amplification of Loci HUMCSF1PO, HUMTPOX, HUMTH01, and HUMCD4

In this example, a DNA template was amplified at the loci HUMCSF1PO, HUMTPOX, HUMTH01, and HUMCD4 simultaneously in a single reaction vessel. The PCR amplifications and other manipulations were performed as described in Example 1 using 0.04 U Taq DNA Polymerase/µl and amplification protocol 1, as described in Example 1. Eight primers were used in combination, including 1 µM each HUMCSF1PO primers 1 [SEQ. ID. 5] and 2 [SEQ. ID. 6], 1 µM each HUMTPOX primers 1 [SEQ. ID. 29] and 2 [SEQ. ID. 30], 1 µM each HUMTH01 primers 1 [SEQ. ID. 27] and 2 [SEQ. ID. 28], and 1 µM each HUMCD4 primers 1 [SEQ. ID. 9] and 2 [SEQ. ID. 10].

Figure 23:
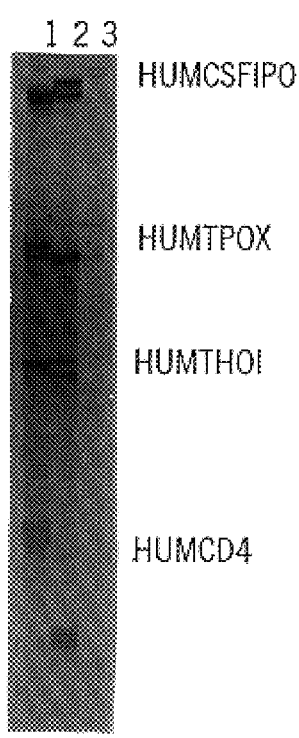
FIG. 23 is a photograph showing the silver stain detection of the multiplex amplification in Example 23.

Reference is made to FIG. 23 which reveals the silver stain detection of the multiplex amplification. Lanes 1–3 contain DNA samples simultaneously co-amplified for the loci HUMCSF1PO, HUMTPOX, HUMTH01, and HUMCD4.

Example 24

Multiplex Amplification of Loci HUMF13A01 and HUMMYOPK (Myotonic)

In this example, a DNA template was amplified at the loci HUMF13A01 and HUMMYOPK (Myotonic) simultaneously in a single reaction vessel. The PCR amplifications and other manipulations were performed as described in Example 1 using 0.04 U Taq DNA Polymerase/µl and amplification protocol 1, as described in Example 1. Four primers were used in combination, including 0.1 µM each HUMF13A01 primers 1 [SEQ. ID. 11] and 2 [SEQ. ID. 12] and 1 µM each HUMMYOPK (Myotonic) primers 1 [SEQ. ID. 21] and 2 [SEQ. ID. 22].

Figure 24:
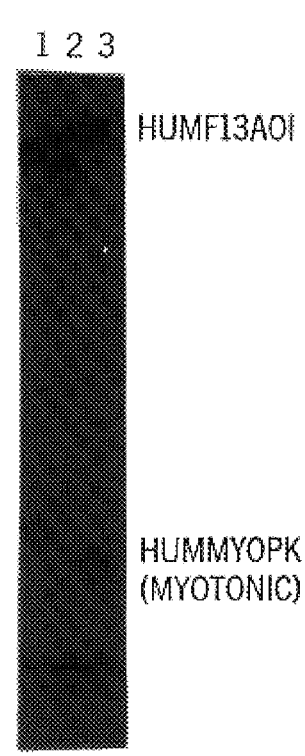
FIG. 24 is a photograph showing the silver stained detection of the multiplex amplification in example 24.

Reference is made to FIG. 24 which reveals the silver stain detection of the multiplex amplification. Lanes 1–3 contain DNA samples simultaneously co-amplified for the loci HUMF13A01 and HUMMYOPK (Myotonic).

Example 25

Multiplex Amplification of Loci HUMF13A01 and HUMBFXIII (F13B)

In this example, a DNA template was amplified at the loci HUMF13A01 and HUMBFXIII (F13B) simultaneously in a single reaction vessel. The PCR amplifications and other manipulations were performed as described in Example 1 using 0.03 U Taq DNA Polymerase/µl and amplification protocol 2, as described in Example 3. Four primers were used in combination, including 0.1 µM each HUMF13A01 primers 1 [SEQ. ID. 11] and 2 [SEQ. ID. 12] and 0.5 µM each HUMBFXIII (F13B) primers 1 [SEQ. ID. 13] and 2 [SEQ. ID. 14].

Figure 25:
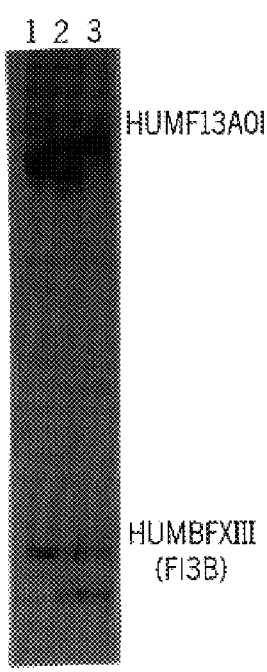
FIG. 25 is a photograph showing the silver stain detection of the multiplex amplification in Example 25.

Reference is made to FIG. 25 which reveals the silver stain detection of the multiplex amplification. Lanes 1–3 contain DNA samples simultaneously co-amplified for the loci HUMF13A01 and HUMBFXIII (F13B).

Example 26

Fluorescent Detection of Multiplex Amplification of Loci HUMCSF1PO, HUMTPOX, HUMTH01, and HUMCD4

In this example, a DNA template was amplified at the individual loci HUMCSF1PO, HUMTPOX, HUMTH01, and HUMCD4 simultaneously in a single reaction vessel. The PCR amplifications were performed as described in Example 1 using 0.04 U Taq DNA Polymerase/µl and amplification protocol 1, as described in Example 1. Eight amplification primers were used in combination, including 2 µM each HUMCSF1PO primer 2 [SEQ. ID. 6] and fluorescein-labeled primer 1 [SEQ. ID. 5], 0.5 µM each HUMTPOX primer 1 [SEQ. ID. 29] and fluorescein-labeled primer 2 [SEQ. ID. 30], 0.5 µM each HUMTH01 primer 2 [SEQ. ID. 28] and fluorescein-labeled primer 1 [SEQ. ID. 27] and 0.5 µM each HUMCD4 primer 1 [SEQ. ID. 9] and fluorescein-labeled primer 2 [SEQ. ID. 10].

Figure 26:
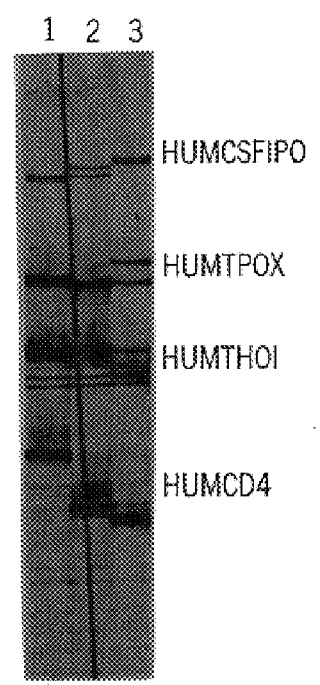
FIG. 26 is a photograph of a computer image showing the fluorescent detection of the multiplex amplification in Example 26.

Amplified products were detected as in Example 2. Reference is made to FIG. 26 which is a photograph of a computer image of a FluorImager scan. Lanes 1–3 contain DNA samples simultaneously co-amplified for the loci HUMCSF1PO, HUMTPOX, HUMTH01, and HUMCD4.

Example 27

Fluorescent Detection of Multiplex Amplification of Loci HUMCSF1PO, HUMTH01, and HUMCD4

In this example, a DNA template was amplified at the individual loci HUMCSF1PO, HUMTH01, and HUMCD4 simultaneously in a single reaction vessel. The PCR amplifications were performed as described in Example 1 using 0.02 U Taq DNA Polymerase/µl and amplification protocol 1, as described in Example 1. Six amplification primers were used in combination, including 1 µM each HUMCSF1PO primer 2 [SEQ. ID. 6] and fluorescein-labeled primer 1 [SEQ. ID. 5], 1 µM each HUMTH01 primer 2 [SEQ. ID. 28] and fluorescein-labeled primer 1 [SEQ. ID. 27] and 1 µM each HUMCD4 primer 1 [SEQ. ID. 9] and fluorescein-labeled primer 2 [SEQ. ID. 10].

Figure 27:
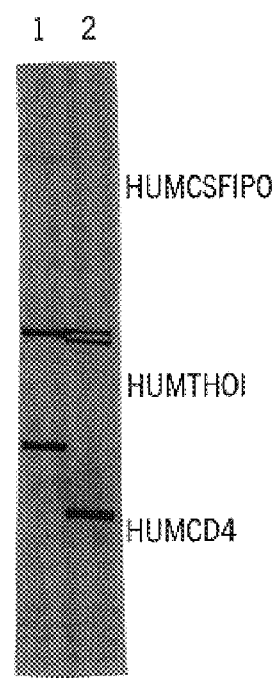
FIG. 27 is a photograph of a computer image showing the fluorescent detection of the multiplex amplification in Example 27.

Amplified products were detected as in Example 2. Reference is made to FIG. 27 which is a photograph of a computer image of a FluorImager scan. Lanes 1 and 2 contain DNA samples simultaneously co-amplified for the loci HUMCSF1PO, HUMTH01, and HUMCD4.

Example 28

Fluorescent Detection of Multiplex Amplification of Loci HUMCSF1PO, HUMTH01, and HUMVWFA31

In this example, a DNA template was amplified at the individual loci HUMCSF1PO, HUMTH01, and HUMVWFA31 simultaneously in a single reaction vessel. The PCR amplifications were performed as described in Example 1 using 0.02 U Taq DNA Polymerase/µl and amplification protocol 1, as described in Example 1. Six amplification primers were used in combination, including 1 µM each HUMCSF1PO primer 2 [SEQ. ID. 6] and fluorescein-labeled primer 1 [SEQ. ID. 5], 1 µM each HUMTH01 primer 2 [SEQ. ID. 28] and fluorescein-labeled primer 1 [SEQ. ID. 27], and 1 µM each HUMVWFA31 primer 1 [SEQ. ID. 31] and fluorescein-labeled primer 2 [SEQ. ID. 32].

Figure 28:
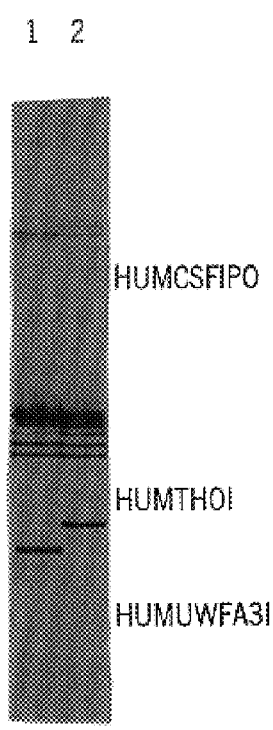
FIG. 28 is a photograph of a computer image showing the fluorescent detection of the multiplex amplification in Example 28.

Amplified products were detected as in Example 2. Reference is made to FIG. 28 which is a photograph of a computer image of a FluorImager scan. Lanes 1 and 2 contain DNA samples simultaneously co-amplified for the loci HUMCSF1PO, HUMTH01, and HUMVWFA31.

Example 29

Fluorescent Detection of Multiplex Amplification of Loci HUMHPRTB, HUMBFXIII (F13B), and HUMLIPOL In this example, a DNA template was amplified at the individual loci HUMHPRTB, HUMBFXIII (F13B), and HUMLIPOL simultaneously in a single reaction vessel. The PCR amplifications were performed as described in Example 1 using 0.03 U Taq DNA Polymerase/µl and amplification protocol 2, as described in Example 3. Six amplification primers were used in combination, including 1 µM each HUMHPRTB primer 2 [SEQ. ID. 20] and fluorescein-labeled primer 1 [SEQ. ID. 19], 1 µM each HUMBFXIII (F13B) primer 2 [SEQ. ID. 14] and fluorescein-labeled primer 1 [SEQ. ID. 13], and 1 µM each HUMLIPOL primer 2 [SEQ. ID. 24] and fluorescein-labeled primer 1 [SEQ. ID. 23].

Figure 29:
FIG. 29 is a photograph of a computer image showing the fluorescent detection of the multiplex amplification in Example 29.

Amplified products were detected as in Example 2. Reference is made to FIG. 29 which is a photograph of a computer image of a FluorImager scan. Lanes 1–3 contain DNA samples simultaneously co-amplified for the loci HUMHPRTB, HUMBFXIII (F13B), and HUMLIPOL.

Example 30

Fluorescent Detection of Multiplex Amplification of Loci HUMCSF1PO and HUMTH01

In this example, a DNA template was amplified at the individual loci HUMCSF1PO and HUMTH01 simultaneously in a single reaction vessel. The PCR amplifications were performed as described in Example 1 using 0.02 U Taq DNA Polymerase/µl and amplification protocol 1, as described in Example 1. Four amplification primers were used in combination, including 2 µM each HUMCSF1PO primer 2 [SEQ. ID. 6] and fluorescein-labeled primer 1 [SEQ. ID. 5] and 1 µM each HUMTH01 primer 2 [SEQ. ID. 28] and fluorescein-labeled primer 1 [SEQ. ID. 27].

Figure 30:
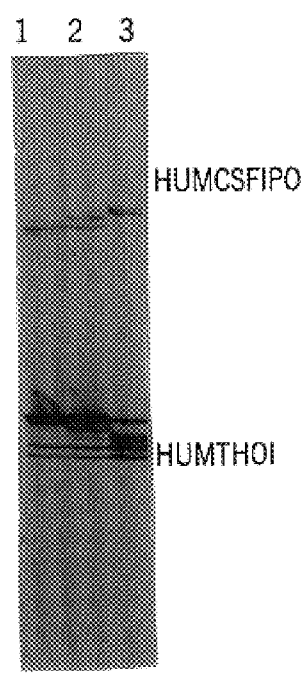
FIG. 30 is a photograph of a computer image showing the fluorescent detection of the multiplex amplification in Example 30.

Amplified products were detected as in Example 2. Reference is made to FIG. 30 which is a photograph of a computer image of a FluorImager scan. Lanes 1–3 contain DNA samples simultaneously co-amplified for the loci HUMCSF1PO and HUMTH01.

Example 31

Fluorescent Detection of Multiplex Amplification of Loci HUMTH01 and HUMCD4

In this example, a DNA template was amplified at the individual loci HUMTH01 and HUMCD4 simultaneously in a single reaction vessel. The PCR amplifications were performed as described in Example 1 using 0.02 U Taq DNA Polymerase/µl and amplification protocol 1, as described in Example 1. Four amplification primers were used in combination, including 1 µM each HUMTH01 primer 2 [SEQ. ID. 28] and fluorescein-labeled primer 1 [SEQ. ID. 27] and 1 µM each HUMCD4 primer 1 [SEQ. ID. 9] and fluorescein-labeled primer 2 [SEQ. ID. 10].

Figure 31:
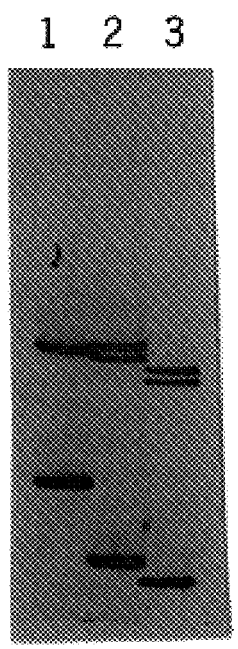
FIG. 31 is a photograph of a computer image showing the fluorescent detection of the multiplex amplification in Example 31.

Amplified products were detected as in Example 2. Reference is made to FIG. 31 which is a photograph of a computer image of a FluorImager scan. Lanes 1–3 contain DNA samples simultaneously co-amplified for the loci HUMTH01 and HUMCD4.

Example 32

Fluorescent Detection of Multiplex Amplification of Loci HUMTH01 and HUMTPOX

In this example, a DNA template was amplified at the individual loci HUMTH01 and HUMTPOX simultaneously in a single reaction vessel. The PCR amplifications were performed as described in Example 1 using 0.02 U Taq DNA Polymerase/µl and amplification protocol 1, as described in Example 1. Four amplification primers were used in combination, including 1 µM each HUMTH01 primer 2 [SEQ. ID. 28] and fluorescein-labeled primer 1 [SEQ. ID. 27] and 1 µM each HUMTPOX primer 2 [SEQ. ID. 30] and fluorescein-labeled primer 1 [SEQ. ID. 29].

Figure 32:
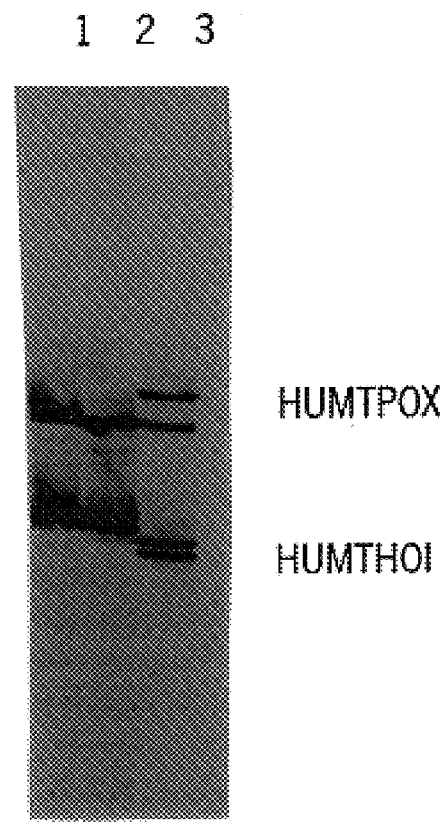
FIG. 32 is a photograph of a computer image showing the fluorescent detection of the multiplex amplification in Example 32.

Amplified products were detected as in Example 2. Reference is made to FIG. 32 which is a photograph of a computer image of a FluorImager scan. Lanes 1–3 contain DNA samples simultaneously co-amplified for the loci HUMTH01 and HUMTPOX.

It is understood that the invention is not confined to the particular construction and arrangements herein illustrated and described, but embraces such modified forms thereof and come within the scope of the claims following the bibliography.

BIBLIOGRAPHY

Alford, R. L., et al. (1994) "Rapid and efficient resolution of parentage by amplification of short tandem repeats," *Am J. Hum Genet*. 55: 190–195.

Ballabio, A. et al. (1991) "PCR Tests for Cystic Fibrosis Deletion." *Nature*, 343: 220.

Bassam, B. J., et al. (1991) "Fast and sensitive silver staining of DNA in polyacrylamide gels," *Anal. Biochem.* 196: 80–83.

Beckman, J. S., and Weber, J. L. (1992) "Survey of human and rat microsatellites," *Genomics* 12: 627–631.

Beggs, A. H., et al. (1990) "Detection of 98% DMD/BMD gene deletions by PCR," *Hum. Genet.* 86: 45–48.

Brunk C. F., et al. 4(1979) "Assay for nanogram quantities of DNA in cellular homogenates," *Anal Biochem* 92: 497–500.

Chakraborty R (1993) "A class of population genetic questions formulated as the generalized occupancy problem." *Genetics* 134: 953–958.

Chamberlain, J. S., et al. (1988) "Deletion screening of the Duchenne muscular dystrophy locus via multiplex DNA amplification," *Nucleic Acid Res.* 16: 11141–11156.

Chamberlain, J. S., et al. (1989), "Multiple PCR for the diagnosis of Duchenne muscular dystrophy," In *PCR Protocols, A Guide to Methods and Application* (ed. Gelfand, D. H., et al.) pp.272–281. Academic Press, San Diego, Calif.

Clemens, P. R., et al. (1991). "Carrier detection and prenatal diagnosis in Duchenne and Becker muscular dystrophy families, using dinucleotide repeat polymorphisms," *Am J. Hum. Genet.* 49: 951–960.

Covone, A. E., et al. (1992) "Screening Duchenne and Becker muscular dystrophy patients for deletions in 30 exons of the dystrophin gene by three-multiplex PCR," *Am. J. Hum. Genet.* 51: 675–677.

Edwards, A., et al. (1991) "DNA typing and genetic mapping with trimeric and tetrameric tandem repeats," *Am. J. Hum. Genet.* 49: 746–756.

Edwards, A., et al. (1992) "Genetic variation at five trimeric and tetrameric tandem repeat loci in four human population groups," *Genomics* 12: 241–253.

Edwards, M. C., and Gibbs, R. A. (1994) "Multiplex PCR: Advantages, development, and applications," *PCR Methods and Applications* 3: S65–S75.

Estivill, X., et al. (1991) "Prenatal diagnosis of cystic fibrosis by multiplex PCR of mutation and microsatellite alleles," *Lancet* 338: 458.

Ferrie, R. M., et al. (1992) "Development, multiplexing, and application of ARMS tests for common mutations in the CFTR gene," *Am. J. Hum. Genet.* 51: 251–262.

Fortina, P., et al. (1992) "Non-radioactive detection of the most common mutations in the cystic fibrosis transmembrane conductance regulator gene by multiplex polymerase chain reaction," *Hum Genet.* 90: 375–378.

Fregeau, C. J., and Fourney, R. M. (1993) "DNA typing with fluorescently tagged short tandem repeats: A sensitive and accurate approach to human identification," *BioTechniques* 15(1): 100–119.

Gibbs, R. A., et al. (1990) "Multiple DNA deletion detection and exon sequencing of the hypoxanthine phosphoribosyltransferase gene in Lesch-Nyhan families," *Genomics* 7: 235–244.

Gill P, et al. (1985) "Forensic application of DNA 'fingerprints'," *Nature* 318: 577–579.

Hammond, H. A., et al. (1994) "Evaluation of 13 STR loci for use in personal identification applications," *Am. J. Hum. Genet.* 55: 175–189.

Huang, T. H.-M., et al. (1992) "Genetic mapping of four dinucleotide repeat loci DXS435, DXS45, DXS454, DXS424, on the X chromosome using the multiplex polymerase chain reaction," *Genomics* 13: 375–380.

Kimpton, C. P., et al. (1993) "Automated DNA profiling employing multiplex amplification of short tandem repeat loci," *PCR Methods and Applications* 3: 13–22.

Kobayashi Y. (1988) "A method to cast thin sequencing gels." *BRL Focus* 10: 73–74.

Litt, M. and Luty, J. A. (1989) "A hypervariable microsatellite revealed by in-vitro amplification of a dinucleotide repeat within the cardiac muscle actin gene," *Am. J. Hum. Genet.* 44: 397–401.

Lohmann, D., et al. (1992) "Detection of small RB1 gene deletions in retinoblastoma by multiplex PCR and high-resolution gel electrophoresis," *Hum. Genet.* 89: 49–53.

Morral, N. and Estivill, X. (1992) "Multiplex PCR amplification of three microsatellites within the CFTR gene," *Genomics* 51: 1362–1364.

Nakamura Y., et al. (1987) "Variable number of tandem repeat (VNTR) markers for human gene mapping," *Science* 235: 1616–1622.

Patel PI, et al. (1984) "Organization of the HPRT gene and related sequences in the human genome," *Somat Cell Mol Genet* 10: 483–493.

Puers C. et al. (1993) "Identification of repeat sequence heterogeneity at the polymorphic short tandem repeat locus HUMTH01 [AATG]$_n$ and reassignment of alleles in population analysis by using a locus-specific allelic ladder,"*Am J Hum Genet* 53: 953–958.

Sambrook J. et al. (1989) In "Molecular cloning—A laboratory manual," 2nd edition, Cold Spring Harbor Laboratory Press.

Schumm, J. W. et al. (1994) "Development of nonisotopic multiplex amplification sets for analysis of polymorphic STR loci," in "The Fourth International Symposium on Human Identification 1993," pp. 177–187.

Schwartz, J. S., et al. (1992) "Fluorescent multiple linkage analysis and carrier detection for Duchenne/Becker's muscular dystrophy," *Am J. Hum. Genet.* 51: 721–729.

Tautz, D., et al. (1986) "Cryptic simplicity in DNA is a major source of genetic variation," *Nature* 322: 652–656.

Weber, J. L. and May, P. E. (1989) "Abundant class of human DNA polymorphisms which can be typed using the polymerase chain reaction," *Am. J. Hum. Genet.* 44: 388–396.

---

What is claimed is:

1. A method of simultaneously determining the alleles present in at least three short tandem repeat loci from one or more DNA samples, comprising:
   a) obtaining at least one DNA sample to be analyzed;
   b) selecting a set of at least three short tandem repeat loci of the DNA sample to be analyzed which can be co-amplified, wherein the at least three short tandem repeat loci in the set comprises at least three loci selected from the group consisting of:
   HUMPOX, HUMTH01 and HUMCD4;
   HUMTPOX, HUMTH01 and HUMVWFA31;
   HUMHPRTB, HUMFESFPS and HUMVWFA31;

HSAC04 (ACTBP2), HUMCYP19 and HUMPLA2A1;
HUMAPOA2, HUMCYP19 and HUMPLA2A1;
HUMCD4, HUMCSF1PO and HUMTH01;
HUMCYP19, HUMFABP and HUMPLA2A1;
HUMCYP19, HUMHPRTB and HUMPLA2A1;
HUMHPRTB, HUMFESFPS and HUMLIPOL;
HUMF13AO1, HUMFABP and HUMCD4;
HUMHPRTB, HUMBFXIII (F13B) and HUMPLA2A1;
HUMHPRTB, HUMBFXIII (F13B) and HUMTPOX;
HUMHPRTB, HUMBFXIII (F13B) and HUMFESFPS;
HUMCSF1PO, HUMTPOX and HUMCD4;
HUMHPRTB, HUMFESFPS and HUMMYOPK (Myotonic);
HUMCSF1PO, HUMTH01 and HUMCD4;
HUMCSF1PO, HUMTH01 and HUMVWFA31; and
HUMHPRTB, HUMBFXIII (F13B) and HUMLIPOL;

c) co-amplifying the set of at least three short tandem repeat loci in a multiplex amplification reaction, thereby producing a mixture of amplified alleles from each of the co-amplified loci in the set; and d) evaluating the amplified alleles in the mixture to determine the alleles present at each of the co-amplified loci in the set.

2. The method of claim 1 wherein in step (b), the at least three loci are co-amplified by multiplex polymerase chain reaction.

3. The method of claim 1 wherein the at least three loci are co-amplified using at least one oligonucleotide primer pair consisting of two oligonucleotide primers, at least one of which has a sequence selected from a group of sequences consisting of:

SEQ ID. NO. 1 and SEQ ID. NO. 2 when one of the loci in the set is HSAC04;
SEQ ID. NO. 3 and SEQ ID. NO. 4 when one of the loci in the set is HUMAPOA2;
SEQ ID. NO. 5 and SEQ ID. NO. 6 when one of the loci in the set is HUMCSF1PO;
SEQ ID. NO. 7 and SEQ ID. NO. 8 when one of the loci in the set is HUMCYP19;
SEQ ID. NO. 9 and SEQ ID. NO. 10 when one of the loci in the set is HUMCD4;
SEQ ID. NO. 11 and SEQ ID. NO. 12 when one of the loci in the set is HUMF13A01;
SEQ ID. NO.13 and SEQ ID. NO. 14 when one of the loci in the set is HUMBFXIII;
SEQ ID. NO. 15 and SEQ ID. NO. 16 when one of the loci in the set is HUMFABP;
SEQ ID. NO. 17 and SEQ ID. NO. 18 when one of the loci in the set is HUMFESFPS;
SEQ ID. NO. 19 and SEQ ID. NO. 20 when one of the loci in the set is HUMHPRTB;
SEQ ID. NO. 21 and SEQ ID. NO. 22 when one of the loci in the set is HUMMYOPK (Myotonic);
SEQ ID. NO. 23 and SEQ ID. NO. 24 when one of the loci in the set is HUMLIPOL;
SEQ ID. NO. 25 and SEQ ID. NO. 26 when one of the loci in the set is HUMPLA2A1;
SEQ ID. NO. 27 and SEQ ID. NO. 28 when one of the loci in the set is HUMTH01;
SEQ ID. NO. 29 and SEQ ID. NO. 30 when one of the loci in the set is HUMTPOX; and
SEQ ID. NO. 31 and SEQ ID. NO. 32 when one of the loci in the set is HUMVWFA31.

4. The method of claim 1, wherein the amplified alleles are evaluated in step (d) by separating the alleles and comparing the separated alleles to a size standard selected from a DNA size marker or a locus-specific allelic ladder.

5. The method of claim 1, further comprising the step of separating the alleles by denaturing polyacrylamide gel electrophoresis.

6. The method of claim 5 wherein the separated alleles are detected by silver staining.

7. The method of claim 5 wherein the separated alleles are detected by fluorescence detection.

8. The method of claim 1, further comprising:
identifying primers for co-amplifying each locus in the set of loci selected in step (b) such that the amplified alleles produced in the multiplex amplification reaction of step (c) do not overlap when separated to evaluate the amplified alleles in step (e); and
using the primers in the multiplex amplification reaction in step (c).

9. The method of claim 1 wherein the at least one DNA sample to be analyzed is selected from the group consisting of blood, semen, vaginal cells, hair, saliva, urine or other tissue, placental cells or fetal cells present in amniotic fluid and mixtures of body fluids.

10. A kit for simultaneously analyzing short tandem repeat sequences in at least three loci, comprising:
a single container containing oligonucleotide primers for each locus in a set of at least three short tandem repeat loci, wherein the at least three short tandem repeat loci in the set comprises at least three loci selected from the group consisting of:
HUMTPOX, HUMTH01 and HUMCD4;
HUMTPOX, HUMTH01 and HUMVWFA31;
HUMTPOX, HUMVWFA31 and HUMCSF1PO;
HUMHPRTB, HUMFESFPS and HUMVWFA31;
HSAC04 (ACTBP2), HUMCYP19 and HUMPLA2A1;
HUMAPOA2, HUMCYP19 and HUMPLA2A1;
HUMCD4, HUMCSF1PO and HUMTH01;
HUMCYP19, HUMFABP and HUMPLA2A1;
HUMCYP19, HUMHPRTB and HUMPLA2A1;
HUMHPRTB, HUMFESFPS and HUMLIPOL;
HUMF13AO1, HUMFABP and HUMCD4;
HUMHPRTB, HUMBFXIII (F13B) and HUMPLA2A1;
HUMHPRTB, HUMBFXIII (F13B) and HUMTPOX;
HUMHPRTB, HUMBFXIII (F13B) and HUMFESFPS;
HUMBFXIII (F13B), HUMFESFPS and HUMLIPOL;
HUMCSF1PO, HUMTPOX and HUMCD4;
HUMBRTB, HUMFESFPS and HUMMYOPK (Myotonic);
HUMCSF1PO, HUMTH01 and HUMCD4;
HUMCSF1PO, HUMTH01 and HUMVWFA31; and
HUMHPRTB, HUMBFXIII (F13B) and HUMLIPOL.

11. The kit of claim 10 wherein each of the oligonucleotide primers in the kit is designed to hybridize with an allele of one of the loci in the set of at least two short tandem repeat loci, wherein the sequence of at least one of the primers is selected from the group consisting of:

SEQ ID. NO. 1 and SEQ ID. NO. 2 when one of the loci in the set is HSAC04;
SEQ ID. NO. 3 and SEQ ID. NO. 4 when one of the loci in the set is HUMAPOA2;

SEQ ID. NO. 5 and SEQ ID. NO. 6 when one of the loci in the set is HUMCSF1PO;

SEQ ID. NO. 7 and SEQ ID. NO. 8 when one of the loci in the set is HUMCYP19;

SEQ ID. NO. 9 and SEQ ID. NO. 10 when one of the loci in the set is HUMCD4;

SEQ ID. NO. 11 and SEQ ID. NO. 12 when one of the loci in the set is HUMF13A01;

SEQ ID. NO. 13 and SEQ ID. NO. 14 when one of the loci in the set is HUMBFXIII;

SEQ ID. NO. 15 and SEQ ID. NO. 16 when one of the loci in the set is HUMFABP;

SEQ ID. NO. 17 and SEQ ID. NO. 18 when one of the loci in the set is HUMFESFPS;

SEQ ID. NO. 19 and SEQ ID. NO. 20 when one of the loci in the set is HUMBPRTB;

SEQ ID. NO. 21 and SEQ ID. NO. 22 when one of the loci in the set is HUMMYOPK (Myotonic);

SEQ ID. NO. 23 and SEQ ID. NO. 24 when one of the loci in the set is HUMLIPOL;

SEQ ID. NO. 25 and SEQ ID. NO. 26 when one of the loci in the set is HUMPLA2A1;

SEQ ID. NO. 27 and SEQ ID. NO. 28 when one of the loci in the set is HUMTH01;

SEQ ID. NO. 29 and SEQ ID. NO. 30 when one of the loci in the set is HUMTPOX; and SEQ ID. NO. 31 and SEQ ID. NO. 32 when one of the loci in the set is HUMVWFA31.

12. A method of simultaneously determining the alleles present in a set of short tandem repeat loci from one or more DNA samples, comprising:

a) obtaining at least one DNA sample to be analyzed;

b) selecting a set of short tandem repeat loci of the DNA sample to be analyzed which can be co-amplified, comprising HUMCSF1PO, HUMTPOX, and HUMTH01;

c) co-amplifying the set of short tandem repeat loci in a multiplex amplification reaction, thereby producing a mixture of amplified alleles from each of the co-amplified loci in the set; and d) evaluating the amplified alleles in the mixture to determine the alleles present at each of the co-amplified loci in the set.

13. The method of claim 12, wherein the multiplex reaction is carried out using oligonucleotide primer pairs with primer pair sequences comprising: SEQ ID. NO. 5 and SEQ ID. NO. 6; SEQ ID. NO. 29 and SEQ ID. NO. 30; and SEQ ID. NO. 27 and SEQ ID. NO. 28.

14. The method of claim 12, wherein the oligonucleotide primer pairs having the sequences SEQ ID. NO. 5 and SEQ ID. NO. 6, and SEQ ID. NO. 29 and SEQ ID. NO. 30 are present in a concentration of about 0.2 $\mu$M, and the oligonucleotide primer pairs SEQ ID. NO. 27 and SEQ ID. NO. 28 are present in a concentration of about 0.6 $\mu$M.

15. The method of claim 12, wherein the set of loci co-amplified further comprises HUMVWFA31.

16. The method of claim 12, wherein the multiplex reaction is carried out using oligonucleotide primer pairs with primer pair sequences comprising: SEQ ID. NO. 5 and SEQ ID. NO. 6, SEQ ID. NO. 29 and SEQ ID. NO. 30, SEQ ID. NO. 27 and SEQ ID. NO. 28, and SEQ ID. NO. 31 and SEQ ID. NO. 32.

17. The method of claim 16, wherein the oligonucleotide primer pairs SEQ ID. NO. 5 and SEQ ID. NO. 6 are present in a concentration of about 1 $\mu$M; oligonucleotide primer pairs SEQ ID. NO. 29 and SEQ ID. NO. 30 are present in a concentration of about 0.15 $\mu$M, oligonucleotide primer pairs SEQ ID. NO. 27 and SEQ ID. NO. 28 are present in a concentration of about 0.2 $\mu$M, and oligonucleotide primer pair SEQ ID. NO. 31 and SEQ ID. NO. 32 are present in a concentration of about 1 $\mu$M.

18. The method of claim 12, wherein the amplified alleles are separated by denaturing polyacrylamide gel electrophoresis, and detected by silver staining.

19. The method of claim 12, wherein the multiplex amplification reaction includes oligonucleotide primers for each locus in the set of loci selected in step (b), wherein at least one of the oligonucleotide primers for each locus is fluorescently labeled.

20. The method of claim 12, wherein the set of loci co-amplified further comprises HUMCD4.

21. The method of claim 12, wherein the set of loci co-amplified further comprises HUMVWFA31.

22. The method of claim 12, wherein the amplified alleles are separated by denaturing polyacrylamide gel electrophoresis, and detected by fluorescent detection.

23. A kit for simultaneously analyzing short tandem repeat sequences in a set of short tandem repeat loci from one or more DNA samples, comprising:

a single container containing oligonucleotide primers for each locus in a set of short tandem repeat loci which can be co-amplified, comprising HUMCSF1PO, HUMTPOX, and HUMTH01.

24. The kit of claim 23, wherein the kit contains oligonucleotide primers designed to co-amplify the set of short tandem repeat loci, further comprising HUMVWFA31.

25. The kit of claim 23, wherein the kit contains oligonucleotide primers designed to co-amplify the set of short tandem repeat loci, further comprising HUMCD4.

26. The kit of claim 23, wherein each of the oligonucleotide primers in the kit is designed to hybridize with an allele of one of the loci in the set of at least three short tandem repeat loci, wherein at least one of the oligonucleotide primers in the kit has a sequence selected from the group consisting of: SEQ ID. NO. 5, SEQ ID. NO. 6, SEQ ID. NO. 29, SEQ ID. NO. 30, SEQ ID. NO. 27, and SEQ ID. NO. 28.

27. The kit of claim 23, wherein one of each of the pair of oligonucleotide primers in the kit is fluorescently-labeled.

28. A method of simultaneously determining the alleles present in a set of short tandem repeat loci from one or more DNA samples, comprising:

a) obtaining at least one DNA sample to be analyzed;

b) selecting a set of short tandem repeat loci of the DNA sample to be analyzed which can be co-amplified, comprising HUMTPOX, HUMVWFA31, and HUMCSF1PO;

c) co-amplifying the set of short tandem repeat loci in a multiplex amplification reaction, thereby producing a mixture of amplified alleles from each of the co-amplified loci in the set; and d) evaluating the amplified alleles in the mixture to determine the alleles present at each of the co-amplified loci in the set.

29. The method of claim 28, wherein the multiplex reaction is carried out using oligonucleotide primer pairs with at least one primer pair selected from the group of primer pair sequences consisting of: SEQ ID. NO. 29 and SEQ ID. NO. 30; SEQ ID. NO. 31 and SEQ ID. NO. 32; and SEQ ID. NO. 5 and SEQ ID. NO. 6.

30. The method of claim 28, wherein the amplified alleles are separated by denaturing polyacrylamide gel electrophoresis, and detected by silver staining.

31. The method of claim 28, wherein the amplified alleles are separated by denaturing polyacrylamide gel electrophoresis, and detected by fluorescent analysis.

32. The method of claim 31, wherein the multiplex amplification reaction includes oligonucleotide primers for each locus in the set of loci selected in step (b), wherein at least one of the oligonucleotide primers for each locus is fluorescently labeled.

33. A kit for simultaneously analyzing short tandem repeat sequences in a set of short tandem repeat loci from one or more DNA samples, comprising:

a single container containing oligonucleotide primers for each locus in a set of short tandem repeat loci which can be co-amplified, comprising HUMTPOX, HUMVWFA31, and HUMCSF1PO.

34. The kit of claim 33, wherein each of the oligonucleotide primers in the kit is designed to hybridize with an allele of one of the loci in the set of at least three short tandem repeat loci, wherein at least one of the oligonucleotide primers in the kit has a sequence selected from the group consisting of: SEQ ID. NO. 29 and SEQ ID. NO. 30; SEQ ID. NO. 31 and SEQ ID. NO. 32; and SEQ ID. NO. 5 and SEQ ID. NO. 6.

35. A method of simultaneously determining the alleles present in a set of short tandem repeat loci from one or more DNA samples, comprising:

a) obtaining at least one DNA sample to be analyzed;

b) selecting a set of short tandem repeat loci of the DNA sample to be analyzed which can be co-amplified, comprising HUMBFXIII (F13B), HUMFESFPS, and HUMLIPOL;

c) co-amplifying the set of short tandem repeat loci in a multiplex amplification reaction, thereby producing a mixture of amplified alleles from each of the co-amplified loci in the set; and d) evaluating the amplified alleles in the mixture to determine the alleles present at each of the co-amplified loci in the set.

36. The method of claim 35, wherein the multiplex reaction is carried out using oligonucleotide primer pairs with at least one primer pair selected from the group of primer pair sequences consisting of: SEQ ID. NO. 13 and SEQ ID. NO. 14; SEQ ID. NO. 17 and SEQ ID. NO. 18; and SEQ ID. NO. 23 and SEQ ID. NO. 24.

37. The method of claim 35, wherein the set of short tandem repeat loci selected for multiplex amplification further comprises HUMHPRTB.

38. The method of claim 35, wherein the amplified alleles are separated by denaturing polyacrylamide gel electrophoresis, and detected by silver staining.

39. The method of claim 35, wherein the amplified alleles are separated by denaturing polyacrylamide gel electrophoresis, and detected by fluorescent analysis.

40. The method of claim 35, wherein the multiplex amplification reaction includes oligonucleotide primers for each locus in the set of loci selected in step (b), wherein at least one of the oligonucleotide primers for each locus is fluorescently labeled.

41. A kit for simultaneously analyzing short tandem repeat sequences in a set of short tandem repeat loci from one or more DNA samples, comprising:

a single container containing oligonucleotide primers for each locus in a set of short tandem repeat loci which can be co-amplified, comprising HUMBFXIII (F13B), HUMFESFPS, and HUMLIPOL.

42. The kit of claim 41, wherein each of the oligonucleotide primers in the kit is designed to hybridize with an allele of one of the loci in the set of at least three short tandem repeat loci, wherein at least one of the oligonucleotide primers in the kit has a sequence selected from the group consisting of: SEQ ID. NO. 13 and SEQ ID. NO. 14; SEQ ID. NO. 17 and SEQ ID. NO. 18; and SEQ ID. NO. 23 and SEQ ID. NO. 24.

43. The kit of claim 41, wherein the kit contains oligonucleotide primers designed to co-amplify the set of short tandem repeat loci, further comprising HUMHPRTB.

* * * * *

UNITED STATES PATENT AND TRADEMARK OFFICE
CERTIFICATE OF CORRECTION

PATENT NO. : 6,221,598 B1
DATED : April 24. 2001
INVENTOR(S) : James W. Schumm et al.

It is certified that error appears in the above-identified patent and that said Letters Patent is hereby corrected as shown below:

Column 12,
Line 20, "DATP" should read -- dATP --.

Column 13,
Line 66, "DATP" should read -- dATP --.

Column 15,
Line 1, "DATP" should read -- dATP --.

Column 38,
Line 53, "HUMBRTB" should read -- HUMHPRTB --.

Column 39,
Line 17, "HUMBPRTB" should read -- HUMHPRTB --.

Signed and Sealed this

Eleventh Day of December, 2001

Attest:

NICHOLAS P. GODICI
*Attesting Officer*     *Acting Director of the United States Patent and Trademark Office*

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

ACATCTCCCC TACCGCTATA       20

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
AATCTGGGCG ACAAGAGTGA                                           20
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
GGAGCAGTCC TAGGGCCGCG CCGT                                      24
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
GTGACAGAGG GAGACTCCAT TAAA                                      24
```

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
AACCTGAGTC TGCCAAGGAC TAGC                                      24
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
TTCCACACAC CACTGGCCAT CTTC                                      24
```

(2) INFORMATION FOR SEQ ID NO: 7:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCAGGTACTT AGTTAGCTAC                                           20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

TTACAGTGAG CCAAGGTCGT                                           20

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CCAGGAAGTT GAGGCTGCAG TGAA                                      24

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

TTGGAGTCGC AAGCTGAACT AGCG                                      24

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GAGGTTGCAC TCCAGCCTTT GCAA                                      24

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

TTCCTGAATC ATCCCAGAGC CACA                                                    24

(2) INFORMATION FOR SEQ ID NO: 13:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 13:

TGAGGTGGTG TACTACCATA                                                         20

(2) INFORMATION FOR SEQ ID NO: 14:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 14:

GATCATGCCA TTGCACTCTA                                                         20

(2) INFORMATION FOR SEQ ID NO: 15:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 15:

GTAGTATCAG TTTCATAGGG TCACC                                                   25

(2) INFORMATION FOR SEQ ID NO: 16:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 16:

CAGTTCGTTT CCATTGTCTG TCCG                                                    24

(2) INFORMATION FOR SEQ ID NO: 17:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 17:

GCTGTTAATT CATGTAGGGA AGGC                                              24

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GTAGTCCCAG CTACTTGGCT ACTC                                              24

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

ATGCCACAGA TAATACACAT CCCC                                              24

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CTCTCCAGAA TAGTTAGATG TAGG                                              24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GCTCGAAGGG TCCTTGTAGC CGGG                                              24

(2) INFORMATION FOR SEQ ID NO: 22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

GATAGGTGGG GGTGCGTGGA GGAT                                              24

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

CTGACCAAGG ATAGTGGGAT ATAG        24

(2) INFORMATION FOR SEQ ID NO: 24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GGTAACTGAG CGAGACTGTG TCT        23

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

GGTTGTAAGC TCCATGAGGT TAGA        24

(2) INFORMATION FOR SEQ ID NO: 26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

TTGAGCACTT ACTATGTGCC AGGCT        25

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

GTGGGCTGAA AAGCTCCCGA TTAT        24

(2) INFORMATION FOR SEQ ID NO: 28:

(i) SEQUENCE CHARACTERISTICS:
        (A) LENGTH: 24 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

ATTCAAAGGG TATCTGGGCT CTGG                                          24

(2) INFORMATION FOR SEQ ID NO: 29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

ACTGGCACAG AACAGGCACT TAGG                                          24

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

GGAGGAACTG GGAACCACAC AGGT                                          24

(2) INFORMATION FOR SEQ ID NO: 31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

GAAAGCCCTA GTGGATGATA AGAATAATC                                     29

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

GGACAGATGA TAAATACATA GGATGGATGG                                    30
```